(12) United States Patent
Steube

(10) Patent No.: US 8,926,563 B2
(45) Date of Patent: Jan. 6, 2015

(54) SAFETY IV CATHETER ASSEMBLIES

(71) Applicant: Gregory A. Steube, St. Charles, MO (US)

(72) Inventor: Gregory A. Steube, St. Charles, MO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/939,553

(22) Filed: Jul. 11, 2013

(65) Prior Publication Data

US 2014/0018738 A1 Jan. 16, 2014

Related U.S. Application Data

(63) Continuation of application No. 13/457,550, filed on Apr. 27, 2012, now Pat. No. 8,486,024.

(60) Provisional application No. 61/479,556, filed on Apr. 27, 2011.

(51) Int. Cl.
*A61M 25/06* (2006.01)
*A61M 5/32* (2006.01)

(52) U.S. Cl.
CPC ......... *A61M 25/0618* (2013.01); *A61M 5/3273* (2013.01)
USPC .................. 604/164.08; 604/162

(58) Field of Classification Search
CPC ............... A61M 25/0618; A61M 25/0612; A61M 2005/325
USPC .............. 128/919; 604/162, 164.08, 198, 263
See application file for complete search history.

(56) References Cited

U.S. PATENT DOCUMENTS

| | | |
|---|---|---|
| 3,134,380 A | 5/1964 | Armao |
| 3,884,230 A | 5/1975 | Wulff |
| 4,387,879 A | 6/1983 | Tauschinski |
| 4,512,766 A | 4/1985 | Vailancourt |
| 4,725,267 A | 2/1988 | Vaillancourt |
| 4,755,170 A | 7/1988 | Golden |
| 4,778,453 A | 10/1988 | Lopez |
| 4,795,432 A | 1/1989 | Karczmer |
| 4,804,370 A | 2/1989 | Haber |
| 4,804,371 A | 2/1989 | Vaillancourt |
| 4,808,169 A | 2/1989 | Haber |

(Continued)

FOREIGN PATENT DOCUMENTS

| | | |
|---|---|---|
| EP | 0352928 | 1/1990 |
| EP | 0475375 | 3/1992 |

(Continued)

OTHER PUBLICATIONS

European Search Report dated Jul. 26, 2012 in copending European Appln. No. 12165851.

(Continued)

*Primary Examiner* — Nicholas Lucchesi
*Assistant Examiner* — Gerald Landry, II
(74) *Attorney, Agent, or Firm* — Lisa E. Winsor, Esq.

(57) ABSTRACT

A safety IV catheter assembly is disclosed which includes a catheter assembly, a needle assembly and a needle guard assembly. The needle guard assembly includes a needle guard, a biasing member and a bushing. The bushing is slidably positioned about the needle and includes an inner diameter which is smaller than an enlarged diameter portion of the needle such that the needle cannot be withdrawn through the bore of the bushing.

10 Claims, 6 Drawing Sheets

(56) References Cited

U.S. PATENT DOCUMENTS

| | | | |
|---|---|---|---|
| 4,834,718 A | 5/1989 | Mc donald |
| 4,842,591 A | 6/1989 | Luther |
| 4,846,805 A | 7/1989 | Sitar |
| 4,850,977 A | 7/1989 | Bayless |
| 4,850,994 A | 7/1989 | Zerbst |
| 4,863,434 A | 9/1989 | Bayless |
| 4,863,436 A | 9/1989 | Glick |
| 4,867,746 A | 9/1989 | Dufresne |
| 4,874,377 A | 10/1989 | Newgard |
| 4,908,022 A | 3/1990 | Haber |
| 4,909,794 A | 3/1990 | Haber |
| 4,911,706 A | 3/1990 | Levitt |
| 4,917,668 A | 4/1990 | Haindl |
| 4,921,486 A | 5/1990 | De chellis |
| 4,921,490 A | 5/1990 | Spier |
| 4,927,415 A | 5/1990 | Brodsky |
| 4,929,241 A | 5/1990 | Kulli |
| 4,931,040 A | 6/1990 | Haber |
| 4,935,010 A | 6/1990 | Cox |
| 4,944,723 A | 7/1990 | Haber |
| 4,944,725 A | 7/1990 | McDonald |
| 4,944,728 A | 7/1990 | Carrell |
| 4,952,207 A | 8/1990 | Lemieux |
| 4,955,866 A | 9/1990 | Corey |
| 4,964,854 A | 10/1990 | Luther |
| 4,978,343 A | 12/1990 | Dysarz |
| 4,978,344 A | 12/1990 | Dombrowski |
| 4,986,813 A | 1/1991 | Blake, III |
| 4,986,819 A | 1/1991 | Sobel |
| 4,994,041 A | 2/1991 | Dombrowski |
| 4,994,046 A | 2/1991 | Wesson |
| 4,998,922 A | 3/1991 | Kuracina |
| 5,002,533 A | 3/1991 | Jullien |
| 5,013,305 A | 5/1991 | Opie |
| 5,015,234 A | 5/1991 | Jullien |
| 5,015,240 A | 5/1991 | Soproni |
| 5,015,241 A | 5/1991 | Feimer |
| 5,015,242 A | 5/1991 | Heifetz |
| 5,030,208 A | 7/1991 | Novacek |
| 5,049,136 A | 9/1991 | Johnson |
| 5,051,109 A | 9/1991 | Simon |
| 5,053,014 A | 10/1991 | Van heugten |
| 5,053,017 A * | 10/1991 | Chamuel ........................ 604/192 |
| 5,059,180 A | 10/1991 | Mclees |
| 5,059,184 A | 10/1991 | Dyke |
| 5,080,651 A | 1/1992 | Julien |
| 5,084,018 A | 1/1992 | Tsao |
| 5,085,648 A | 2/1992 | Purdy |
| 5,092,461 A | 3/1992 | Adam |
| 5,092,851 A | 3/1992 | Ragner |
| 5,104,378 A | 4/1992 | Haber |
| 5,112,311 A | 5/1992 | Utterberg |
| 5,114,404 A | 5/1992 | Paxton |
| 5,120,321 A | 6/1992 | Oksman |
| 5,122,118 A | 6/1992 | Haber |
| 5,122,124 A | 6/1992 | Novacek |
| 5,127,905 A | 7/1992 | Lemieux |
| 5,131,405 A | 7/1992 | Burns |
| 5,135,504 A | 8/1992 | Mc lees |
| 5,137,515 A | 8/1992 | Hogan |
| 5,147,327 A | 9/1992 | Johnson |
| 5,154,699 A | 10/1992 | Ryan |
| 5,154,703 A | 10/1992 | Bonaldo |
| 5,156,596 A | 10/1992 | Balbierz |
| 5,158,554 A | 10/1992 | Jepson |
| 5,169,391 A | 12/1992 | Vogel |
| 5,171,229 A | 12/1992 | Mc neil |
| 5,171,300 A | 12/1992 | Blake, III |
| 5,176,650 A | 1/1993 | Haining |
| 5,176,655 A | 1/1993 | Mc cormick |
| 5,176,656 A | 1/1993 | Bayless |
| 5,180,369 A | 1/1993 | Dysarz |
| 5,180,370 A | 1/1993 | Gillespie |
| 5,183,468 A | 2/1993 | Mclees |
| 5,188,607 A | 2/1993 | Wu |
| 5,195,723 A | 3/1993 | Schauerte |
| 5,195,974 A | 3/1993 | Hardy |
| 5,195,980 A | 3/1993 | Catlin |
| 5,199,947 A | 4/1993 | Lopez |
| 5,205,827 A | 4/1993 | Novacek |
| 5,205,829 A | 4/1993 | Lituchy |
| 5,207,656 A | 5/1993 | Kranys |
| 5,211,629 A | 5/1993 | Pressly |
| 5,211,633 A | 5/1993 | Stouder, Jr. |
| 5,215,525 A | 6/1993 | Sturman |
| 5,215,528 A | 6/1993 | Purdy |
| 5,215,533 A | 6/1993 | Robb |
| 5,215,534 A | 6/1993 | De harde |
| 5,215,538 A | 6/1993 | Larkin |
| 5,222,505 A | 6/1993 | Burns |
| 5,224,936 A | 7/1993 | Gallagher |
| 5,228,646 A | 7/1993 | Raines |
| 5,232,456 A | 8/1993 | Gonzalez |
| 5,232,458 A | 8/1993 | Chen |
| 5,234,410 A | 8/1993 | Graham |
| 5,242,393 A | 9/1993 | Brimball |
| 5,242,400 A | 9/1993 | Blake, III |
| 5,242,402 A | 9/1993 | Chen |
| 5,242,411 A | 9/1993 | Yamamoto |
| 5,246,427 A | 9/1993 | Sturman |
| RE34,416 E | 10/1993 | Lemieux |
| 5,251,873 A | 10/1993 | Atkinson |
| 5,254,099 A | 10/1993 | Kuracina |
| 5,256,152 A | 10/1993 | Marks |
| 5,261,880 A | 11/1993 | Streck |
| 5,261,894 A | 11/1993 | Smith |
| 5,263,933 A | 11/1993 | Novacek |
| 5,266,072 A | 11/1993 | Utterberg |
| 5,267,966 A | 12/1993 | Paul |
| 5,267,976 A | 12/1993 | Guerineau |
| 5,269,763 A | 12/1993 | Boehmer |
| 5,269,764 A | 12/1993 | Vetter |
| 5,269,765 A | 12/1993 | Kuracina |
| 5,269,771 A | 12/1993 | Thomas |
| 5,273,540 A | 12/1993 | Luther |
| 5,277,342 A | 1/1994 | Dickau |
| 5,279,570 A | 1/1994 | Dombrowski |
| 5,279,571 A | 1/1994 | Larkin |
| 5,279,591 A | 1/1994 | Simon |
| 5,290,246 A | 3/1994 | Yamamoto |
| 5,293,970 A | 3/1994 | Schneider |
| 5,295,657 A | 3/1994 | Atkinson |
| 5,295,658 A | 3/1994 | Atkinson |
| 5,295,963 A | 3/1994 | Deeks |
| 5,295,972 A | 3/1994 | Mischenko |
| 5,297,777 A | 3/1994 | Yie |
| 5,300,032 A | 4/1994 | Hibbs |
| 5,300,033 A | 4/1994 | Miller |
| 5,300,034 A | 4/1994 | Behnke |
| 5,300,035 A | 4/1994 | Clement |
| 5,300,040 A | 4/1994 | Martin |
| 5,300,045 A | 4/1994 | Plassche, Jr. |
| 5,304,136 A | 4/1994 | Erskine |
| 5,304,151 A | 4/1994 | Kuracina |
| 5,304,156 A | 4/1994 | Sylvanowicz |
| 5,306,243 A | 4/1994 | Bonaldo |
| 5,308,336 A | 5/1994 | Hart |
| 5,312,355 A | 5/1994 | Lee |
| 5,312,362 A | 5/1994 | Pfolsgraf |
| 5,312,363 A | 5/1994 | Ryan |
| 5,312,371 A | 5/1994 | Dombrowski |
| 5,312,372 A | 5/1994 | De harde |
| 5,322,517 A | 6/1994 | Sircom |
| 5,322,518 A | 6/1994 | Schneider |
| 5,324,271 A | 6/1994 | Abiuso |
| 5,328,478 A | 7/1994 | Mcvay |
| 5,328,482 A | 7/1994 | Sircom |
| 5,328,484 A | 7/1994 | Somers |
| 5,328,485 A | 7/1994 | Moreno |
| 5,330,435 A | 7/1994 | Vaillancourt |
| 5,330,437 A | 7/1994 | Durman |
| 5,334,158 A | 8/1994 | Mclees |
| 5,334,159 A | 8/1994 | Turkel |
| 5,336,192 A | 8/1994 | Palestrant |

(56) References Cited

U.S. PATENT DOCUMENTS

| | | |
|---|---|---|
| 5,336,198 A | 8/1994 | Silver |
| 5,336,199 A | 8/1994 | Castillo |
| 5,336,200 A | 8/1994 | Streck |
| 5,342,316 A | 8/1994 | Wallace |
| 5,342,319 A | 8/1994 | Watson |
| 5,344,161 A | 9/1994 | Sandgren |
| 5,344,408 A | 9/1994 | Partika |
| 5,344,414 A | 9/1994 | Lopez |
| 5,348,544 A | 9/1994 | Sweeney |
| 5,350,362 A | 9/1994 | Stouder, Jr. |
| 5,350,363 A | 9/1994 | Goode |
| 5,352,205 A | 10/1994 | Dales |
| 5,353,837 A | 10/1994 | Faust |
| 5,354,280 A | 10/1994 | Haber |
| 5,356,384 A | 10/1994 | Haber |
| 5,360,413 A | 11/1994 | Leason |
| 5,364,370 A | 11/1994 | Szerlip |
| 5,364,372 A | 11/1994 | Danks |
| 5,368,574 A | 11/1994 | Antonacci |
| 5,376,077 A | 12/1994 | Gomringer |
| 5,380,288 A | 1/1995 | Hart |
| 5,380,305 A | 1/1995 | Ghouri |
| 5,382,235 A | 1/1995 | Sak |
| 5,383,860 A | 1/1995 | Lau |
| 5,385,550 A | 1/1995 | Su |
| 5,389,081 A | 2/1995 | Castro |
| 5,390,898 A | 2/1995 | Smedley |
| 5,395,338 A | 3/1995 | Gaba |
| 5,395,346 A | 3/1995 | Maggioni |
| 5,395,347 A | 3/1995 | Blecher |
| 5,395,352 A | 3/1995 | Penny |
| 5,403,284 A | 4/1995 | Gross |
| 5,405,323 A | 4/1995 | Rogers |
| 5,405,327 A | 4/1995 | Chen |
| 5,405,331 A | 4/1995 | Behnke |
| 5,409,461 A | 4/1995 | Steinman |
| 5,409,464 A | 4/1995 | Villalobos |
| 5,411,486 A | 5/1995 | Zadini |
| 5,411,492 A | 5/1995 | Sturman |
| 5,415,638 A | 5/1995 | Novacek |
| 5,417,659 A | 5/1995 | Gaba |
| 5,417,673 A | 5/1995 | Gordon |
| 5,419,766 A | 5/1995 | Chang |
| 5,423,766 A | 6/1995 | Cesare |
| 5,425,718 A | 6/1995 | Tay |
| 5,425,720 A | 6/1995 | Rogalsky |
| 5,429,596 A | 7/1995 | Arias |
| 5,429,619 A | 7/1995 | Furnish |
| 5,431,631 A | 7/1995 | Lu |
| 5,431,632 A | 7/1995 | Lu |
| 5,433,703 A | 7/1995 | Utterberg |
| 5,437,646 A | 8/1995 | Hunt |
| 5,439,451 A | 8/1995 | Collinson |
| 5,441,487 A | 8/1995 | Vedder |
| 5,443,452 A | 8/1995 | Hart |
| 5,443,454 A | 8/1995 | Tanabe |
| 5,447,501 A | 9/1995 | Karlsson |
| 5,453,095 A | 9/1995 | Davila |
| 5,454,790 A | 10/1995 | Dubrul |
| 5,456,284 A | 10/1995 | Ryan |
| 5,456,675 A | 10/1995 | Wolbring |
| 5,458,640 A | 10/1995 | Gerrone |
| 5,458,658 A | 10/1995 | Sircom |
| 5,460,603 A | 10/1995 | Desantis |
| 5,462,531 A | 10/1995 | Novacek |
| 5,465,938 A | 11/1995 | Werge |
| 5,466,223 A | 11/1995 | Bressler |
| 5,466,230 A | 11/1995 | Davila |
| 5,470,319 A | 11/1995 | Mayer |
| 5,472,418 A | 12/1995 | Palestrant |
| 5,474,544 A | 12/1995 | Lynn |
| 5,478,313 A | 12/1995 | White |
| 5,480,393 A | 1/1996 | Bommarito |
| 5,484,401 A | 1/1996 | Rodriguez |
| 5,486,190 A | 1/1996 | Green |
| 5,487,728 A | 1/1996 | Vaillancourt |
| 5,487,733 A | 1/1996 | Caizza |
| 5,487,850 A | 1/1996 | Vanderploeg |
| 5,489,274 A | 2/1996 | Chu |
| 5,492,147 A | 2/1996 | Challender |
| 5,492,304 A | 2/1996 | Smith |
| 5,496,274 A | 3/1996 | Graves |
| 5,496,280 A | 3/1996 | Vandenbroek |
| 5,501,426 A | 3/1996 | Atkinson |
| 5,501,670 A | 3/1996 | Sak |
| 5,501,675 A | 3/1996 | Erskine |
| 5,507,732 A | 4/1996 | Mcclure |
| 5,509,433 A | 4/1996 | Paradis |
| 5,514,098 A | 5/1996 | Pfoslgraf |
| 5,514,116 A | 5/1996 | Vaillancourt |
| 5,514,117 A | 5/1996 | Lynn |
| 5,520,649 A | 5/1996 | Novacek |
| 5,520,655 A | 5/1996 | Davila |
| 5,520,666 A | 5/1996 | Choudhury |
| 5,531,701 A | 7/1996 | Luther |
| 5,533,974 A | 7/1996 | Gaba |
| 5,533,975 A | 7/1996 | Lu |
| 5,535,785 A | 7/1996 | Werge |
| 5,538,505 A | 7/1996 | Weinstein |
| 5,538,508 A | 7/1996 | Steyn |
| 5,540,661 A | 7/1996 | Tomisaka |
| 5,540,662 A | 7/1996 | Nicholson |
| 5,545,146 A | 8/1996 | Ishak |
| 5,545,152 A | 8/1996 | Funderburk |
| 5,549,565 A | 8/1996 | Ryan |
| 5,549,566 A | 8/1996 | Elias |
| 5,549,570 A | 8/1996 | Rogalsky |
| 5,549,576 A | 8/1996 | Patterson |
| 5,549,651 A | 8/1996 | Lynn |
| 5,554,131 A | 9/1996 | Lacivita |
| 5,558,651 A | 9/1996 | Crawford |
| 5,562,629 A | 10/1996 | Haughton |
| 5,562,630 A | 10/1996 | Nichols |
| 5,562,632 A | 10/1996 | Davila |
| 5,562,633 A | 10/1996 | Wozencroft |
| 5,562,636 A | 10/1996 | Utterberg |
| 5,562,637 A | 10/1996 | Utterberg |
| 5,569,202 A | 10/1996 | Kovalic |
| 5,569,203 A | 10/1996 | Chen |
| 5,569,205 A | 10/1996 | Hart |
| 5,569,209 A | 10/1996 | Roitman |
| 5,569,288 A | 10/1996 | Yoon |
| 5,573,545 A | 11/1996 | Yoon |
| 5,575,774 A | 11/1996 | Chen |
| 5,575,777 A | 11/1996 | Davidner |
| 5,575,804 A | 11/1996 | Yoon |
| 5,578,059 A | 11/1996 | Patzer |
| 5,582,594 A | 12/1996 | Chen |
| 5,582,597 A | 12/1996 | Brimhall |
| 5,584,808 A | 12/1996 | Healy |
| 5,584,809 A | 12/1996 | Gaba |
| 5,584,810 A | 12/1996 | Brimhall |
| 5,584,818 A | 12/1996 | Morrison |
| 5,584,848 A | 12/1996 | Yoon |
| 5,584,849 A | 12/1996 | Yoon |
| 5,584,850 A | 12/1996 | Hart |
| 5,588,966 A | 12/1996 | Atsumi |
| 5,591,134 A | 1/1997 | Shu |
| 5,591,137 A | 1/1997 | Stevens |
| 5,591,190 A | 1/1997 | Yoon |
| 5,591,193 A | 1/1997 | Yoon |
| 5,599,310 A | 2/1997 | Bogert |
| 5,601,532 A | 2/1997 | Gaba |
| 5,601,534 A | 2/1997 | Turner |
| 5,601,536 A | 2/1997 | Crawford |
| 5,607,396 A | 3/1997 | Yoon |
| 5,607,439 A | 3/1997 | Yoon |
| 5,611,781 A | 3/1997 | Sircom |
| 5,611,792 A | 3/1997 | Gustafsson |
| 5,613,500 A | 3/1997 | Bishop |
| 5,613,663 A | 3/1997 | Schmidt |
| 5,613,952 A | 3/1997 | Pressly, Sr. |
| 5,613,954 A | 3/1997 | Nelson |
| 5,613,956 A | 3/1997 | Patterson |

(56) References Cited

U.S. PATENT DOCUMENTS

| | | | |
|---|---|---|---|
| 5,616,129 | A | 4/1997 | Mayer |
| 5,616,130 | A | 4/1997 | Mayer |
| 5,618,271 | A | 4/1997 | Yoon |
| 5,630,803 | A | 5/1997 | Tamaro |
| 5,634,913 | A | 6/1997 | Stinger |
| 5,634,934 | A | 6/1997 | Yoon |
| 5,643,227 | A | 7/1997 | Stevens |
| 5,645,076 | A | 7/1997 | Yoon |
| 5,645,533 | A | 7/1997 | Blaeser |
| 5,651,772 | A | 7/1997 | Arnett |
| 5,653,698 | A | 8/1997 | Niedospial |
| 5,662,610 | A | 9/1997 | Sircom |
| 5,669,891 | A | 9/1997 | Vaillancourt |
| 5,672,160 | A | 9/1997 | Osterlind |
| 5,672,161 | A | 9/1997 | Allen |
| 5,676,681 | A | 10/1997 | Yoon |
| 5,676,682 | A | 10/1997 | Yoon |
| 5,676,683 | A | 10/1997 | Yoon |
| 5,683,365 | A | 11/1997 | Brown |
| 5,683,368 | A | 11/1997 | Schmidt |
| 5,685,855 | A | 11/1997 | Erskine |
| 5,685,860 | A | 11/1997 | Chang |
| 5,688,240 | A | 11/1997 | Novacek |
| 5,688,253 | A | 11/1997 | Paradis |
| 5,688,254 | A | 11/1997 | Lopez |
| 5,688,286 | A | 11/1997 | Yoon |
| 5,693,025 | A | 12/1997 | Stevens |
| 5,693,031 | A | 12/1997 | Ryan |
| 5,695,474 | A | 12/1997 | Daugherty |
| 5,696,466 | A | 12/1997 | Li |
| 5,697,907 | A | 12/1997 | Gaba |
| 5,699,821 | A | 12/1997 | Paradis |
| 5,700,249 | A | 12/1997 | Jenkins |
| 5,700,250 | A | 12/1997 | Erskine |
| 5,702,367 | A | 12/1997 | Cover |
| 5,709,664 | A | 1/1998 | Vandenbroek |
| 5,718,688 | A | 2/1998 | Wozencroft |
| 5,718,689 | A | 2/1998 | Stevenson |
| 5,718,691 | A | 2/1998 | Russo |
| 5,720,734 | A | 2/1998 | Copenhaver |
| 5,722,958 | A | 3/1998 | Gravener |
| 5,725,503 | A | 3/1998 | Arnett |
| 5,735,827 | A | 4/1998 | Adwers |
| 5,738,144 | A | 4/1998 | Rogers |
| 5,738,665 | A | 4/1998 | Caizza |
| 5,743,884 | A | 4/1998 | Hasson |
| 5,743,888 | A | 4/1998 | Wilkes |
| 5,743,891 | A | 4/1998 | Tolkoff et al. |
| 5,746,718 | A | 5/1998 | Steyn |
| 5,749,857 | A | 5/1998 | Cuppy |
| 5,749,859 | A | 5/1998 | Powell |
| 5,749,861 | A | 5/1998 | Guala |
| 5,749,889 | A | 5/1998 | Bacich |
| 5,755,699 | A | 5/1998 | Blecher |
| 5,755,701 | A | 5/1998 | Sarstedt |
| 5,772,636 | A | 6/1998 | Brimhall |
| 5,776,113 | A | 7/1998 | Daugherty |
| 5,779,681 | A | 7/1998 | Bonn |
| 5,779,684 | A | 7/1998 | Tamaro |
| 5,782,804 | A | 7/1998 | Mcmahon |
| D397,434 | S | 8/1998 | Pike |
| 5,788,675 | A | 8/1998 | Mayer |
| 5,792,121 | A | 8/1998 | Tamaro |
| 5,795,339 | A | 8/1998 | Erskine |
| 5,797,897 | A | 8/1998 | Jepson |
| 5,800,403 | A | 9/1998 | Pressly, Sr. |
| 5,803,919 | A | 9/1998 | Hart |
| 5,806,831 | A | 9/1998 | Paradis |
| 5,807,350 | A | 9/1998 | Diaz |
| 5,807,352 | A | 9/1998 | Tamaro |
| 5,807,353 | A | 9/1998 | Schmitz |
| 5,810,784 | A | 9/1998 | Tamaro |
| 5,814,018 | A | 9/1998 | Elson |
| 5,817,069 | A | 10/1998 | Arnett |
| 5,817,070 | A | 10/1998 | Tamaro |
| 5,820,606 | A | 10/1998 | Davis |
| 5,820,614 | A | 10/1998 | Erskine |
| 5,820,621 | A | 10/1998 | Yale |
| 5,830,189 | A | 11/1998 | Chang |
| 5,833,670 | A | 11/1998 | Dillon |
| 5,851,196 | A | 12/1998 | Arnett |
| 5,853,393 | A | 12/1998 | Bogert |
| 5,853,399 | A | 12/1998 | Sasaki |
| 5,857,999 | A | 1/1999 | Quick |
| 5,858,000 | A | 1/1999 | Novacek |
| 5,858,007 | A | 1/1999 | Fagan |
| 5,865,806 | A | 2/1999 | Howell |
| 5,871,471 | A | 2/1999 | Ryan |
| 5,879,331 | A | 3/1999 | Osterlind |
| 5,879,337 | A | 3/1999 | Kuracina |
| 5,882,337 | A | 3/1999 | Bogert |
| 5,885,256 | A | 3/1999 | Chern et al. |
| 5,891,093 | A | 4/1999 | Dysarz |
| 5,899,887 | A | 5/1999 | Liu |
| 5,910,130 | A | 6/1999 | Caizza |
| 5,911,705 | A | 6/1999 | Howell |
| 5,911,710 | A | 6/1999 | Barry |
| 5,916,198 | A | 6/1999 | Dillow |
| 5,919,168 | A | 7/1999 | Wheeler |
| 5,919,174 | A | 7/1999 | Hanson |
| 5,925,020 | A | 7/1999 | Nestell |
| 5,935,104 | A | 8/1999 | Janek |
| 5,941,850 | A | 8/1999 | Shah |
| 5,951,515 | A | 9/1999 | Osterlind |
| 5,951,529 | A | 9/1999 | Utterberg |
| 5,954,698 | A | 9/1999 | Pike |
| 5,954,708 | A | 9/1999 | Lopez |
| 5,957,887 | A | 9/1999 | Osterlind |
| 5,957,898 | A | 9/1999 | Jepson |
| 5,967,490 | A | 10/1999 | Pike |
| 5,968,068 | A | 10/1999 | Dehdashtian |
| 5,971,957 | A | 10/1999 | Luther |
| 5,989,224 | A | 11/1999 | Exline |
| 5,993,419 | A | 11/1999 | Lo |
| 5,997,486 | A | 12/1999 | Burek |
| 5,997,507 | A | 12/1999 | Dysarz |
| 6,001,080 | A | 12/1999 | Kuracina |
| 6,004,294 | A | 12/1999 | Brimhall |
| 6,012,213 | A | 1/2000 | Chang |
| 6,015,397 | A | 1/2000 | Elson |
| 6,024,729 | A | 2/2000 | Dehdashtian |
| 6,033,386 | A | 3/2000 | Novacek |
| 6,036,672 | A | 3/2000 | Allen |
| 6,039,302 | A | 3/2000 | Cote, Sr. |
| 6,048,335 | A | 4/2000 | Mayer |
| 6,053,861 | A | 4/2000 | Grossi |
| 6,068,011 | A | 5/2000 | Paradis |
| 6,074,370 | A | 6/2000 | Pressly, Jr. |
| 6,077,244 | A | 6/2000 | Botich |
| 6,079,432 | A | 6/2000 | Paradis |
| 6,080,135 | A | 6/2000 | Van Stokkum |
| 6,080,137 | A | 6/2000 | Pike |
| 6,086,566 | A | 7/2000 | Arnissolle |
| 6,090,074 | A | 7/2000 | Brimhall et al. |
| 6,099,500 | A | 8/2000 | Dysarz |
| 6,099,505 | A | 8/2000 | Ryan |
| 6,102,894 | A | 8/2000 | Dysarz |
| RE36,885 | E | 9/2000 | Blecher |
| 6,117,107 | A | 9/2000 | Chen |
| 6,117,108 | A | 9/2000 | Woehr |
| 6,117,110 | A | 9/2000 | Radmand |
| 6,117,113 | A | 9/2000 | Novacek |
| 6,127,320 | A | 10/2000 | Ooij |
| 6,152,900 | A | 11/2000 | Mayer |
| 6,156,010 | A | 12/2000 | Kuracina |
| 6,159,185 | A | 12/2000 | Tanihata |
| 6,162,196 | A | 12/2000 | Hart |
| 6,171,287 | B1 | 1/2001 | Lynn |
| 6,183,440 | B1 | 2/2001 | Bell |
| 6,183,448 | B1 | 2/2001 | Mayer |
| 6,193,690 | B1 | 2/2001 | Dysarz |
| 6,200,262 | B1 | 3/2001 | Ouchi |
| 6,203,527 | B1 | 3/2001 | Zadini |
| 6,203,533 | B1 | 3/2001 | Ouchi |

(56) References Cited

U.S. PATENT DOCUMENTS

| | | |
|---|---|---|
| 6,206,857 B1 | 3/2001 | Chen |
| 6,210,373 B1 | 4/2001 | Allmon |
| 6,213,978 B1 | 4/2001 | Voyten |
| 6,217,555 B1 | 4/2001 | Hart |
| 6,217,568 B1 | 4/2001 | Jepson |
| 6,221,047 B1 | 4/2001 | Greene |
| 6,221,050 B1 | 4/2001 | Ishida |
| 6,221,056 B1 | 4/2001 | Silverman |
| 6,224,569 B1 | 5/2001 | Brimhall |
| 6,228,060 B1 | 5/2001 | Howell |
| 6,234,999 B1 | 5/2001 | Wemmert |
| 6,235,003 B1 | 5/2001 | Dysarz |
| 6,235,006 B1 | 5/2001 | Dillon |
| 6,241,707 B1 | 6/2001 | Dysarz |
| 6,245,045 B1 | 6/2001 | Stratienko |
| 6,245,048 B1 | 6/2001 | Fangrow |
| 6,254,529 B1 | 7/2001 | Ouchi |
| 6,258,065 B1 | 7/2001 | Dennis |
| 6,261,264 B1 | 7/2001 | Tamaro |
| 6,261,265 B1 | 7/2001 | Mosseri |
| 6,273,869 B1 | 8/2001 | Vaillancourt |
| 6,277,100 B1 | 8/2001 | Raulerson |
| 6,280,419 B1 | 8/2001 | Vojtasek |
| 6,287,278 B1 | 9/2001 | Woehr |
| 6,287,279 B1 | 9/2001 | Siekmann |
| 6,287,280 B1 | 9/2001 | Lampropoulos |
| 6,306,124 B1 | 10/2001 | Jones |
| 6,322,537 B1 | 11/2001 | Chang |
| 6,322,541 B2 | 11/2001 | West |
| 6,342,045 B1 | 1/2002 | Somers |
| 6,344,031 B1 | 2/2002 | Novacek |
| 6,344,033 B1 | 2/2002 | Jepson |
| 6,352,520 B1 | 3/2002 | Miyazaki |
| 6,352,521 B1 | 3/2002 | Prosl |
| 6,358,265 B1 | 3/2002 | Thorne, Jr. |
| 6,379,332 B1 | 4/2002 | Van Landuyt |
| 6,379,333 B1 | 4/2002 | Brimhall |
| 6,379,372 B1 | 4/2002 | Dehdashtian |
| 6,394,983 B1 | 5/2002 | Mayoral |
| 6,402,721 B1 | 6/2002 | Lo |
| 6,406,459 B1 | 6/2002 | Allmon |
| 6,409,703 B1 | 6/2002 | Lu |
| 6,413,236 B1 | 7/2002 | Van Dyke |
| 6,416,499 B2 | 7/2002 | Paul, Jr. |
| 6,425,884 B1 | 7/2002 | Wemmert |
| 6,440,101 B1 | 8/2002 | Grabenkort |
| 6,443,927 B1 | 9/2002 | Cook |
| 6,443,929 B1 | 9/2002 | Kuracina |
| 6,461,328 B2 | 10/2002 | Wang |
| 6,475,194 B2 | 11/2002 | Domici, Jr. |
| 6,485,459 B1 | 11/2002 | Surowitz |
| 6,485,468 B2 | 11/2002 | Vojtasek |
| 6,488,656 B1 | 12/2002 | Wu |
| 6,488,663 B1 | 12/2002 | Steg |
| 6,488,674 B2 | 12/2002 | Becker |
| 6,506,181 B2 | 1/2003 | Meng |
| 6,520,939 B2 | 2/2003 | Lafontaine |
| 6,524,276 B1 | 2/2003 | Halseth |
| 6,524,278 B1 | 2/2003 | Campbell |
| 6,527,747 B2 | 3/2003 | Adams |
| 6,530,903 B2 | 3/2003 | Wang |
| 6,533,759 B1 | 3/2003 | Watson |
| 6,537,259 B1 | 3/2003 | Niermann |
| 6,545,242 B1 | 4/2003 | Butler |
| 6,551,283 B1 | 4/2003 | Guo |
| 6,569,119 B1 | 5/2003 | Haberland |
| 6,572,591 B2 | 6/2003 | Mayer |
| 6,582,402 B1 | 6/2003 | Erskine |
| 6,585,701 B1 | 7/2003 | Dysarz |
| 6,585,704 B2 | 7/2003 | Luther |
| 6,592,555 B1 | 7/2003 | Wen-Pi et al. |
| 6,592,556 B1 | 7/2003 | Thorne |
| 6,595,954 B1 | 7/2003 | Luther |
| 6,595,955 B2 | 7/2003 | Ferguson |
| 6,595,964 B2 | 7/2003 | Finley |
| 6,595,965 B1 | 7/2003 | Utterberg |
| 6,595,981 B2 | 7/2003 | Huet |
| 6,602,240 B2 | 8/2003 | Hermann |
| 6,605,073 B1 | 8/2003 | Pressly, Sr. |
| 6,610,031 B1 | 8/2003 | Chin |
| 6,616,630 B1 | 9/2003 | Woehr |
| 6,616,640 B1 | 9/2003 | Chen |
| 6,620,136 B1 | 9/2003 | Pressly, Sr. |
| 6,623,458 B2 | 9/2003 | Woehr |
| 6,629,959 B2 | 10/2003 | Kuracina |
| 6,632,200 B2 | 10/2003 | Guo |
| 6,632,201 B1 | 10/2003 | Mathias |
| 6,641,564 B1 | 11/2003 | Kraus |
| 6,651,956 B2 | 11/2003 | Miller |
| 6,652,486 B2 | 11/2003 | Bialecki |
| 6,652,490 B2 | 11/2003 | Howell |
| 6,663,592 B2 | 12/2003 | Rhad |
| 6,663,599 B2 | 12/2003 | Osbourne |
| 6,669,666 B2 | 12/2003 | Lu |
| 6,669,681 B2 | 12/2003 | Jepson |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene |
| 6,695,817 B1 | 2/2004 | Fangrow, Jr. |
| 6,699,221 B2 | 3/2004 | Vaillancourt |
| 6,706,022 B1 | 3/2004 | Leinsing |
| 6,709,419 B2 | 3/2004 | Woehr |
| 6,712,791 B2 | 3/2004 | Lui |
| 6,719,726 B2 | 4/2004 | Meng |
| 6,723,073 B2 | 4/2004 | Ley |
| 6,736,798 B2 | 5/2004 | Ohkubo |
| 6,743,199 B2 | 6/2004 | Shue |
| 6,749,588 B1 | 6/2004 | Howell |
| 6,761,704 B2 | 7/2004 | Crawford |
| 6,761,705 B1 | 7/2004 | Chiu |
| 6,761,706 B2 | 7/2004 | Vaillancourt |
| 6,764,468 B1 | 7/2004 | East |
| 6,767,340 B2 | 7/2004 | Willis |
| 6,770,059 B1 | 8/2004 | Spinks |
| 6,773,416 B1 | 8/2004 | Hsu |
| 6,776,774 B2 | 8/2004 | Tansey, Jr. |
| 6,796,962 B2 | 9/2004 | Ferguson |
| 6,796,968 B2 | 9/2004 | Ferguson |
| 6,796,969 B1 | 9/2004 | Andersson |
| 6,802,827 B2 | 10/2004 | Andersson |
| 6,808,161 B1 | 10/2004 | Hishikawa |
| 6,808,509 B1 | 10/2004 | Davey |
| 6,811,545 B2 | 11/2004 | Vaillancourt |
| 6,817,989 B2 | 11/2004 | Svendsen |
| 6,821,266 B2 | 11/2004 | Knepshield |
| 6,824,527 B2 | 11/2004 | Gollobin |
| 6,832,992 B2 | 12/2004 | Wilkinson |
| 6,855,127 B2 | 2/2005 | Nakagami |
| 6,855,130 B2 | 2/2005 | Saulenas |
| 6,860,869 B2 | 3/2005 | Dennis |
| 6,860,871 B2 | 3/2005 | Kuracina |
| 6,863,659 B2 | 3/2005 | Sharpe |
| 6,866,656 B2 | 3/2005 | Tingey |
| 6,878,131 B2 | 4/2005 | Novacek |
| 6,878,134 B2 | 4/2005 | Rogers |
| 6,883,778 B1 | 4/2005 | Newton |
| 6,884,224 B2 | 4/2005 | Dalton |
| 6,886,808 B2 | 5/2005 | Sarno |
| 6,893,423 B2 | 5/2005 | Denolly |
| 6,902,546 B2 | 6/2005 | Ferguson |
| 6,905,483 B2 | 6/2005 | Newby |
| 6,908,459 B2 | 6/2005 | Harding |
| 6,911,018 B2 | 6/2005 | Gordon |
| 6,913,595 B2 | 7/2005 | Mastorakis |
| 6,916,309 B2 | 7/2005 | Fangrow, Jr. |
| 6,916,311 B2 | 7/2005 | Vojtasek |
| 6,918,891 B2 | 7/2005 | Bressler |
| 6,921,382 B2 | 7/2005 | Lee |
| 6,921,386 B2 | 7/2005 | Shue |
| 6,926,698 B2 | 8/2005 | Lin |
| 6,926,700 B2 | 8/2005 | Bressler |
| 6,929,622 B2 | 8/2005 | Chian |
| 6,932,803 B2 | 8/2005 | Newby |

(56) References Cited

U.S. PATENT DOCUMENTS

| | | | |
|---|---|---|---|
| 6,936,031 B2 | 8/2005 | Caleffi |
| 6,936,036 B2 | 8/2005 | Wilkinson |
| 6,942,642 B2 | 9/2005 | Suzuki |
| 6,958,055 B2 | 10/2005 | Donnan |
| 6,972,002 B2 | 12/2005 | Thorne |
| 6,979,314 B2 | 12/2005 | Hsieh |
| 6,981,965 B2 | 1/2006 | Luther |
| 6,984,213 B2 | 1/2006 | Horner |
| 6,986,759 B1 | 1/2006 | Jeremijevic |
| 6,991,215 B2 | 1/2006 | Kiehne |
| RE38,996 E | 2/2006 | Crawford |
| 6,997,902 B2 | 2/2006 | Thorne |
| 7,004,927 B2 | 2/2006 | Ferguson |
| 7,004,934 B2 | 2/2006 | Vaillancourt |
| 7,008,402 B2 | 3/2006 | Ferguson |
| 7,008,404 B2 | 3/2006 | Nakajima |
| 7,014,623 B2 | 3/2006 | Prestidge |
| 7,018,344 B2 | 3/2006 | Bressler |
| 7,018,365 B2 | 3/2006 | Strauss |
| 7,025,721 B2 | 4/2006 | Cohen |
| 7,025,744 B2 | 4/2006 | Utterberg |
| 7,033,339 B1 | 4/2006 | Lynn |
| 7,033,345 B2 | 4/2006 | Lee |
| 7,037,292 B2 | 5/2006 | Carlyon |
| 7,037,303 B2 | 5/2006 | Beaufore |
| 7,060,053 B2 | 6/2006 | Nakashima |
| 7,063,685 B2 | 6/2006 | Rome |
| 7,066,908 B2 | 6/2006 | Kuracina |
| 7,077,824 B2 | 7/2006 | Meyer |
| 7,081,106 B1 | 7/2006 | Guo |
| 7,083,596 B2 | 8/2006 | Saied |
| 7,083,600 B2 | 8/2006 | Meloul |
| 7,101,351 B2 | 9/2006 | Crawford |
| 7,101,353 B2 | 9/2006 | Lui |
| 7,104,970 B2 | 9/2006 | Chen |
| 7,112,191 B2 * | 9/2006 | Daga  ............................ 604/263 |
| 7,125,396 B2 | 10/2006 | Leinsing |
| 7,125,397 B2 | 10/2006 | Woehr |
| 7,147,621 B2 | 12/2006 | Kiehne |
| 7,150,725 B2 | 12/2006 | Wilkinson |
| 7,160,269 B2 | 1/2007 | Woehr |
| 7,172,580 B2 | 2/2007 | Hruska |
| 7,175,610 B2 | 2/2007 | Mori |
| 7,179,244 B2 | 2/2007 | Smith |
| 7,182,734 B2 | 2/2007 | Saulenas |
| 7,186,239 B2 | 3/2007 | Woehr |
| 7,192,433 B2 | 3/2007 | Osypka |
| 7,198,618 B2 | 4/2007 | Ferguson |
| 7,207,975 B2 | 4/2007 | Miller |
| 7,214,208 B2 | 5/2007 | Vaillancourt |
| 7,214,211 B2 | 5/2007 | Woehr |
| 7,226,434 B2 | 6/2007 | Carlyon |
| 7,235,062 B2 | 6/2007 | Brustad |
| 7,238,169 B2 | 7/2007 | Takagi |
| 7,239,169 B2 | 7/2007 | Isa |
| 7,247,148 B2 | 7/2007 | Murashita |
| 7,252,651 B2 | 8/2007 | Haider |
| 7,264,613 B2 | 9/2007 | Woehr |
| 7,291,128 B2 | 11/2007 | Rossi |
| 7,291,130 B2 | 11/2007 | McGurk |
| 7,297,138 B2 | 11/2007 | Fangrow, Jr. |
| 7,300,419 B2 | 11/2007 | Fangrow, Jr. |
| 7,303,548 B2 | 12/2007 | Rhad |
| 7,306,579 B2 | 12/2007 | Fujii |
| 7,309,326 B2 | 12/2007 | Fangrow, Jr. |
| 7,311,693 B2 | 12/2007 | Shekalim |
| 7,311,694 B2 | 12/2007 | Fangrow, Jr. |
| 7,314,462 B2 | 1/2008 | O'Reagan |
| 7,314,463 B2 | 1/2008 | Fangrow, Jr. |
| 7,316,667 B2 | 1/2008 | Lindstrom |
| 7,318,818 B2 | 1/2008 | Yashiro |
| 7,326,189 B2 | 2/2008 | Mori |
| 7,331,934 B2 | 2/2008 | Suresh |
| 7,331,935 B2 | 2/2008 | Barere |
| 7,331,939 B2 | 2/2008 | Fangrow, Jr. |
| 7,341,573 B2 | 3/2008 | Ferguson |
| 7,347,838 B2 | 3/2008 | Kulli |
| 7,347,839 B2 | 3/2008 | Hiejima |
| 7,347,842 B2 | 3/2008 | Thorne |
| 7,354,422 B2 | 4/2008 | Riesenberger |
| 7,357,784 B2 | 4/2008 | Ferguson |
| 7,361,164 B2 | 4/2008 | Simpson |
| 7,371,226 B2 | 5/2008 | Huang |
| 7,371,227 B2 | 5/2008 | Zeiner |
| 7,374,554 B2 | 5/2008 | Menzi |
| 7,387,616 B2 | 6/2008 | Li |
| 7,396,346 B2 | 7/2008 | Nakajima |
| 7,399,293 B2 | 7/2008 | Oyibo |
| 7,407,491 B2 | 8/2008 | Fangrow, Jr. |
| 7,407,495 B2 | 8/2008 | Barere |
| 7,413,562 B2 | 8/2008 | Ferguson |
| 7,422,571 B2 | 9/2008 | Schweikert |
| 7,422,573 B2 | 9/2008 | Wilkinson |
| 7,445,611 B2 | 11/2008 | Osborne |
| 7,458,954 B2 | 12/2008 | Ferguson |
| 7,470,254 B2 | 12/2008 | Basta |
| 7,470,261 B2 | 12/2008 | Lynn |
| 7,470,262 B2 | 12/2008 | Hiejima |
| 7,497,847 B2 | 3/2009 | Crawford |
| 7,497,849 B2 | 3/2009 | Fangrow, Jr. |
| 7,500,965 B2 | 3/2009 | Menzi |
| 7,507,222 B2 | 3/2009 | Cindrich |
| 7,513,887 B2 | 4/2009 | Halseth |
| 7,513,888 B2 | 4/2009 | Sircom et al. |
| 7,524,300 B2 | 4/2009 | Patton |
| 7,530,965 B2 | 5/2009 | Villa |
| 7,534,227 B2 | 5/2009 | Kulli |
| 7,534,231 B2 | 5/2009 | Kuracina |
| 7,537,582 B2 | 5/2009 | Suresh |
| 7,544,181 B2 | 6/2009 | Axelsson |
| 7,566,323 B2 | 7/2009 | Chang |
| 7,566,327 B2 | 7/2009 | Mathias |
| 7,569,033 B2 | 8/2009 | Greene |
| 7,572,247 B2 | 8/2009 | Smith |
| 7,575,570 B2 | 8/2009 | Barere |
| 7,578,803 B2 | 8/2009 | Rome |
| 7,578,805 B2 | 8/2009 | Hwang |
| 7,578,806 B2 | 8/2009 | Zeoli |
| 7,591,449 B2 | 9/2009 | Raines |
| 7,597,681 B2 | 10/2009 | Sutton |
| 7,597,684 B2 | 10/2009 | Alchas |
| 7,601,139 B2 | 10/2009 | Woehr |
| 7,604,616 B2 | 10/2009 | Thoresen |
| 7,608,057 B2 | 10/2009 | Woehr |
| 7,611,485 B2 | 11/2009 | Ferguson |
| 7,611,487 B2 | 11/2009 | Woehr |
| 7,611,488 B2 | 11/2009 | Chang |
| 7,611,499 B2 | 11/2009 | Woehr |
| 7,614,423 B2 | 11/2009 | Yokota |
| 7,618,395 B2 | 11/2009 | Ferguson |
| 7,625,360 B2 | 12/2009 | Woehr |
| 7,628,774 B2 | 12/2009 | Fangrow, Jr. |
| 7,628,776 B2 | 12/2009 | Gibson |
| 7,632,243 B2 | 12/2009 | Bialecki |
| 7,635,352 B2 | 12/2009 | Adams |
| 7,635,357 B2 | 12/2009 | Mayer |
| 7,637,887 B2 | 12/2009 | Woehr |
| 7,637,888 B2 | 12/2009 | Schwarzich |
| 7,637,893 B2 | 12/2009 | Christensen |
| 7,651,476 B2 | 1/2010 | Kohler |
| 7,651,481 B2 | 1/2010 | Raybuck |
| 7,654,988 B2 | 2/2010 | Moulton |
| 7,658,725 B2 | 2/2010 | Bialecki |
| 7,662,134 B2 | 2/2010 | Miller |
| 7,666,170 B2 | 2/2010 | Guala |
| 7,670,317 B2 | 3/2010 | Cindrich |
| 7,670,320 B2 | 3/2010 | Iwase |
| 7,682,331 B2 | 3/2010 | Carrez |
| 7,682,339 B2 | 3/2010 | Fujii |
| 7,682,340 B2 | 3/2010 | Funamura |
| 7,686,784 B2 | 3/2010 | Baik |
| 7,691,088 B2 | 4/2010 | Howell |
| 7,694,403 B2 | 4/2010 | Moulton |
| 7,713,242 B2 | 5/2010 | Streifinger |

(56) References Cited

U.S. PATENT DOCUMENTS

| | | |
|---|---|---|
| 7,713,243 B2 | 5/2010 | Hillman |
| 7,713,250 B2 | 5/2010 | Harding |
| 7,713,256 B2 | 5/2010 | Brimhall |
| 7,713,257 B2 | 5/2010 | Brimhall |
| 7,717,888 B2 | 5/2010 | Vaillancourt |
| 7,722,563 B2 | 5/2010 | Isaacson |
| 7,722,564 B2 | 5/2010 | Vaillancourt |
| 7,722,569 B2 | 5/2010 | Soderholm |
| 7,727,198 B2 | 6/2010 | Nakajima |
| 7,731,687 B2 | 6/2010 | Menzi |
| 7,731,694 B2 | 6/2010 | Becker |
| 7,736,332 B2 | 6/2010 | Carlyon |
| 7,736,337 B2 | 6/2010 | Diep |
| 7,736,339 B2 | 6/2010 | Woehr |
| 7,736,340 B2 | 6/2010 | Harding |
| 7,736,342 B2 | 6/2010 | Abriles |
| 7,740,613 B2 | 6/2010 | Yokoi |
| 7,740,614 B2 | 6/2010 | Murashita |
| 7,744,567 B2 | 6/2010 | Glowacki |
| 7,744,568 B2 | 6/2010 | Douglas |
| 7,744,570 B2 | 6/2010 | Fangrow, Jr. |
| 7,753,338 B2 | 7/2010 | Desecki |
| 7,753,877 B2 | 7/2010 | Bialecki |
| 7,753,887 B2 | 7/2010 | Botich |
| 7,758,543 B2 | 7/2010 | Ferraresi |
| 7,762,986 B2 | 7/2010 | Wang |
| 7,763,199 B2 | 7/2010 | Fangrow, Jr. |
| 7,771,412 B2 | 8/2010 | Anderson |
| 7,785,296 B2 | 8/2010 | Muskatello |
| 7,794,445 B2 | 9/2010 | Dalton |
| 7,794,675 B2 | 9/2010 | Lynn |
| 7,798,994 B2 | 9/2010 | Brimhall |
| 7,806,849 B2 | 10/2010 | Woehr |
| 7,806,858 B2 | 10/2010 | Smith |
| 7,806,869 B2 | 10/2010 | Nilsson |
| 7,806,890 B2 | 10/2010 | McKinnon |
| 7,811,261 B2 | 10/2010 | Rubinstein |
| 7,815,614 B2 | 10/2010 | Fangrow, Jr. |
| 7,824,393 B2 | 11/2010 | Fangrow |
| 7,828,773 B2 | 11/2010 | Swisher |
| 7,828,774 B2 | 11/2010 | Harding |
| 7,833,199 B2 | 11/2010 | Franer |
| 7,850,648 B2 | 12/2010 | Gratwohl |
| 7,850,650 B2 | 12/2010 | Breitweiser |
| 7,850,652 B2 | 12/2010 | Liniger |
| 7,867,204 B2 | 1/2011 | Bartholomew |
| 7,887,516 B2 | 2/2011 | Young |
| 7,892,209 B2 | 2/2011 | Harand |
| 7,892,216 B2 | 2/2011 | Fangrow, Jr. |
| 7,901,379 B2 | 3/2011 | Argentine |
| 7,905,857 B2 | 3/2011 | Swisher |
| 7,914,488 B2 | 3/2011 | Dickerson |
| 7,914,494 B2 | 3/2011 | Hiejima |
| 7,914,519 B2 | 3/2011 | Moran |
| 7,922,698 B2 | 4/2011 | Riesenberger |
| 7,927,314 B2 | 4/2011 | Kuracina |
| 7,931,615 B2 | 4/2011 | Fangrow, Jr. |
| 7,931,622 B2 | 4/2011 | Beling |
| 7,935,080 B2 | 5/2011 | Howell |
| 7,935,090 B2 | 5/2011 | Patton |
| 7,938,805 B2 | 5/2011 | Harding |
| 7,947,018 B2 | 5/2011 | Mckinnon |
| 7,947,032 B2 | 5/2011 | Harding |
| 7,951,119 B2 | 5/2011 | Leeflang |
| 7,951,122 B2 | 5/2011 | Shekalim |
| 7,955,306 B2 | 6/2011 | Wyss |
| 7,959,613 B2 | 6/2011 | Rhad |
| 7,967,797 B2 | 6/2011 | Winsor |
| 7,972,300 B2 | 7/2011 | Smith |
| 7,972,313 B2 | 7/2011 | Woehr |
| 7,976,498 B2 | 7/2011 | Swisher |
| 7,976,502 B2 | 7/2011 | Baid |
| 7,976,503 B2 | 7/2011 | Khan |
| 7,981,090 B2 | 7/2011 | Plishka |
| 7,985,199 B2 | 7/2011 | Kornerup |
| 7,985,232 B2 | 7/2011 | Potter |
| 7,988,664 B2 | 8/2011 | Fiser |
| 7,993,305 B2 | 8/2011 | Ye |
| 7,993,306 B2 | 8/2011 | Marrs |
| 7,998,122 B2 | 8/2011 | Lynn |
| 8,002,765 B2 | 8/2011 | Lopez |
| 8,006,953 B2 | 8/2011 | Bennett |
| 8,016,791 B2 | 9/2011 | Sugiki |
| 8,021,343 B2 | 9/2011 | Nalesso |
| 8,025,646 B2 | 9/2011 | Fukai |
| 8,029,472 B2 | 10/2011 | Leinsing |
| 8,038,647 B2 | 10/2011 | Harding |
| 8,043,263 B2 | 10/2011 | Helgeson |
| 8,043,266 B2 | 10/2011 | Murashita |
| 8,043,316 B2 | 10/2011 | Hardin |
| 8,048,031 B2 | 11/2011 | Shaw |
| 8,048,039 B2 | 11/2011 | Carlyon |
| 8,052,646 B2 | 11/2011 | Schweikert |
| 8,052,647 B2 | 11/2011 | Raulerson |
| 8,052,653 B2 | 11/2011 | Gratwohl |
| 8,062,261 B2 | 11/2011 | Adams |
| 8,066,670 B2 | 11/2011 | Cluff |
| 8,075,529 B2 | 12/2011 | Nakajima |
| RE43,141 E | 1/2012 | Halseth |
| 8,088,104 B2 | 1/2012 | Smith |
| 8,096,973 B2 | 1/2012 | Snow |
| 8,100,857 B2 | 1/2012 | Kuracina |
| 8,100,858 B2 | 1/2012 | Woehr |
| 8,105,276 B2 | 1/2012 | Chen |
| 8,123,738 B2 | 2/2012 | Vaillancourt |
| 8,128,594 B1 | 3/2012 | Chang |
| 8,133,207 B2 | 3/2012 | Wilkinson |
| 8,133,209 B2 | 3/2012 | Guala |
| 8,137,321 B2 | 3/2012 | Argentine |
| 8,147,455 B2 | 4/2012 | Butts |
| 8,157,768 B2 | 4/2012 | Haider |
| 8,162,881 B2 | 4/2012 | Lilley, Jr. |
| 8,162,889 B2 | 4/2012 | Swisher |
| 8,162,904 B2 | 4/2012 | Takano |
| 8,172,773 B2 | 5/2012 | Heske et al. |
| 8,197,452 B2 | 6/2012 | Harding |
| 8,206,355 B2 | 6/2012 | Thorne |
| 8,211,070 B2 | 7/2012 | Woehr |
| 8,226,627 B2 | 7/2012 | Fowles |
| 8,231,525 B2 | 7/2012 | Cohen |
| 8,251,950 B2 | 8/2012 | Albert |
| 8,257,322 B2 | 9/2012 | Koehler |
| 2001/0021821 A1 | 9/2001 | Wang |
| 2001/0021827 A1 | 9/2001 | Ferguson |
| 2001/0039401 A1 | 11/2001 | Ferguson |
| 2002/0010434 A1 | 1/2002 | Larsen |
| 2002/0022803 A1 | 2/2002 | Wemmert |
| 2002/0026154 A1 | 2/2002 | Chang |
| 2002/0065488 A1 | 5/2002 | Suzuki |
| 2002/0065489 A1 | 5/2002 | Novacek |
| 2002/0128604 A1 | 9/2002 | Nakajima |
| 2002/0151850 A1 | 10/2002 | Ferguson |
| 2002/0156428 A1 | 10/2002 | Lee |
| 2003/0060771 A1* | 3/2003 | Bialecki et al. .......... 604/164.08 |
| 2003/0060785 A1 | 3/2003 | Lavean |
| 2003/0105431 A1 | 6/2003 | Howell |
| 2003/0114797 A1 | 6/2003 | Vaillancourt |
| 2003/0125676 A1 | 7/2003 | Swenson |
| 2003/0125677 A1 | 7/2003 | Swenson |
| 2003/0130623 A1 | 7/2003 | Chen |
| 2003/0144627 A1 | 7/2003 | Woehr |
| 2003/0181867 A1 | 9/2003 | Bressler |
| 2003/0181869 A1 | 9/2003 | Swenson |
| 2003/0181870 A1 | 9/2003 | Bressler |
| 2003/0181871 A1 | 9/2003 | Wilkinson |
| 2003/0181875 A1 | 9/2003 | Bressler |
| 2003/0195471 A1 | 10/2003 | Woehr |
| 2003/0195479 A1 | 10/2003 | Kuracina |
| 2003/0199827 A1 | 10/2003 | Thorne |
| 2003/0216687 A1 | 11/2003 | Hwang |
| 2003/0229316 A1 | 12/2003 | Hwang |
| 2004/0006313 A1 | 1/2004 | Chian |
| 2004/0019334 A1 | 1/2004 | Ohkubo |
| 2004/0039333 A1 | 2/2004 | Lee |

(56) References Cited

U.S. PATENT DOCUMENTS

| | | |
|---|---|---|
| 2004/0044313 A1 | 3/2004 | Nakajima |
| 2004/0049155 A1 | 3/2004 | Schramm |
| 2004/0078003 A1 | 4/2004 | Smith |
| 2004/0092871 A1 | 5/2004 | Knepshield |
| 2004/0106903 A1 | 6/2004 | Shue |
| 2004/0116857 A1 | 6/2004 | Kiehne |
| 2004/0122378 A1 | 6/2004 | Hsu |
| 2004/0138628 A1 | 7/2004 | Woehr |
| 2004/0147876 A1 | 7/2004 | Maggioni |
| 2004/0171989 A1 | 9/2004 | Horner |
| 2004/0171995 A1 | 9/2004 | Niermann |
| 2004/0186426 A1 | 9/2004 | Allard |
| 2004/0186427 A1 | 9/2004 | Pok |
| 2004/0186434 A1 | 9/2004 | Harding |
| 2004/0204681 A1 | 10/2004 | Thoresen |
| 2004/0225260 A1 | 11/2004 | Villa |
| 2004/0230164 A1 | 11/2004 | Spinks |
| 2004/0236288 A1 | 11/2004 | Howell |
| 2004/0236289 A1 | 11/2004 | Ferguson |
| 2004/0243060 A1 | 12/2004 | Rossi |
| 2004/0243061 A1* | 12/2004 | McGurk ................ 604/164.08 |
| 2004/0243066 A1 | 12/2004 | Meyer |
| 2004/0243071 A1 | 12/2004 | Suzuki |
| 2005/0004532 A1 | 1/2005 | Woehr |
| 2005/0027263 A1 | 2/2005 | Woehr |
| 2005/0038385 A1 | 2/2005 | Shen |
| 2005/0038399 A1 | 2/2005 | Suzuki |
| 2005/0043691 A1 | 2/2005 | Ferguson |
| 2005/0049554 A1 | 3/2005 | Chueh |
| 2005/0059933 A1 | 3/2005 | Johnson |
| 2005/0070855 A1 | 3/2005 | Ferguson |
| 2005/0075609 A1* | 4/2005 | Latona ................ 604/164.08 |
| 2005/0080378 A1 | 4/2005 | Cindrich |
| 2005/0085745 A1 | 4/2005 | Kitta |
| 2005/0096599 A1 | 5/2005 | Crawford |
| 2005/0119627 A1 | 6/2005 | Crawford |
| 2005/0137528 A1 | 6/2005 | Wilkinson |
| 2005/0137535 A1 | 6/2005 | Gollobin |
| 2005/0159706 A1 | 7/2005 | Wilkinson |
| 2005/0182362 A1 | 8/2005 | Sircom |
| 2005/0215951 A1 | 9/2005 | Saulenas |
| 2005/0234408 A1 | 10/2005 | Chong |
| 2005/0240150 A1 | 10/2005 | Gordon |
| 2005/0267412 A1 | 12/2005 | Wilkinson |
| 2006/0058742 A1 | 3/2006 | Cha |
| 2006/0074384 A1 | 4/2006 | Kohler |
| 2006/0079808 A1 | 4/2006 | Allard |
| 2006/0084916 A1 | 4/2006 | Lo |
| 2006/0106339 A1 | 5/2006 | Mastorakis |
| 2006/0106340 A1 | 5/2006 | Goossens |
| 2006/0116638 A1 | 6/2006 | Woehr |
| 2006/0155245 A1 | 7/2006 | Woehr |
| 2006/0161108 A1 | 7/2006 | Mogensen |
| 2006/0161116 A1 | 7/2006 | Willis |
| 2006/0184115 A1 | 8/2006 | Saied |
| 2006/0189934 A1 | 8/2006 | Kuracina |
| 2006/0200195 A1 | 9/2006 | Yang |
| 2006/0217655 A1 | 9/2006 | Vitullo |
| 2006/0229554 A1 | 10/2006 | Lou |
| 2006/0229556 A1 | 10/2006 | Pressly, Sr. |
| 2006/0229563 A1 | 10/2006 | O'Reagan |
| 2006/0253074 A1 | 11/2006 | Thayer |
| 2006/0253076 A1 | 11/2006 | Butts |
| 2006/0264827 A1 | 11/2006 | Whang |
| 2006/0264828 A1 | 11/2006 | Woehr |
| 2007/0005013 A1 | 1/2007 | Lai |
| 2007/0005014 A1 | 1/2007 | Lin |
| 2007/0016139 A1 | 1/2007 | Breitweiser |
| 2007/0038179 A1 | 2/2007 | Bialecki |
| 2007/0038182 A1 | 2/2007 | Bialecki |
| 2007/0038183 A1 | 2/2007 | Bialecki |
| 2007/0038184 A1 | 2/2007 | Bialecki |
| 2007/0038185 A1 | 2/2007 | Albert |
| 2007/0038186 A1 | 2/2007 | Sutton |
| 2007/0038187 A1 | 2/2007 | Albert |
| 2007/0038188 A1 | 2/2007 | Bialecki |
| 2007/0073221 A1 | 3/2007 | Bialecki |
| 2007/0073222 A1 | 3/2007 | Lilley, Jr. |
| 2007/0073225 A1 | 3/2007 | Lee |
| 2007/0078390 A1 | 4/2007 | Cing-hong |
| 2007/0078397 A1 | 4/2007 | Weststrate |
| 2007/0078404 A1 | 4/2007 | Wu |
| 2007/0078405 A1 | 4/2007 | Lai |
| 2007/0078407 A1 | 4/2007 | Huang |
| 2007/0083162 A1 | 4/2007 | O'Reagan |
| 2007/0083167 A1 | 4/2007 | Smith |
| 2007/0100296 A1 | 5/2007 | Hwang |
| 2007/0100297 A1 | 5/2007 | Woehr |
| 2007/0106231 A1 | 5/2007 | Snow |
| 2007/0118082 A1 | 5/2007 | Mori |
| 2007/0135764 A1 | 6/2007 | Chen |
| 2007/0156093 A1 | 7/2007 | Woehr |
| 2007/0156100 A1 | 7/2007 | Moesli |
| 2007/0161950 A1 | 7/2007 | Carlyon |
| 2007/0179443 A1 | 8/2007 | Johnson aka Mindes |
| 2007/0179446 A1 | 8/2007 | Carrez |
| 2007/0197964 A1 | 8/2007 | Hsu |
| 2007/0197965 A1 | 8/2007 | Hsu |
| 2007/0197966 A1 | 8/2007 | Lee |
| 2007/0197967 A1 | 8/2007 | Lee |
| 2007/0219492 A1 | 9/2007 | Lucas |
| 2007/0232998 A1 | 10/2007 | Yang |
| 2007/0250003 A1 | 10/2007 | Bare |
| 2007/0255212 A1 | 11/2007 | Smith |
| 2007/0270753 A1 | 11/2007 | Kulli |
| 2007/0282268 A1 | 12/2007 | Mayse |
| 2008/0021388 A1 | 1/2008 | Schwarzich |
| 2008/0027381 A1 | 1/2008 | Smith |
| 2008/0065015 A1 | 3/2008 | Fiser |
| 2008/0065025 A1 | 3/2008 | Jenkins |
| 2008/0071213 A1 | 3/2008 | Sircom |
| 2008/0071222 A1 | 3/2008 | Rhad |
| 2008/0086089 A1 | 4/2008 | Isaacson |
| 2008/0097304 A1 | 4/2008 | Thorne |
| 2008/0097342 A1 | 4/2008 | Gordin |
| 2008/0097343 A1 | 4/2008 | Woehr |
| 2008/0097344 A1 | 4/2008 | McKinnon |
| 2008/0097345 A1 | 4/2008 | Ferguson |
| 2008/0103449 A1 | 5/2008 | Murashita |
| 2008/0108944 A1 | 5/2008 | Woehr |
| 2008/0115845 A1 | 5/2008 | Leuliet |
| 2008/0119795 A1 | 5/2008 | Erskine |
| 2008/0140011 A1 | 6/2008 | Hager |
| 2008/0147003 A1 | 6/2008 | Menzi |
| 2008/0154195 A1 | 6/2008 | Huang |
| 2008/0177238 A1 | 7/2008 | Follman |
| 2008/0243086 A1 | 10/2008 | Hager |
| 2008/0249478 A1 | 10/2008 | Ishikura |
| 2008/0249480 A1 | 10/2008 | Riesenberger |
| 2008/0283789 A1 | 11/2008 | Rubio |
| 2008/0312596 A1 | 12/2008 | Murashita |
| 2008/0319387 A1 | 12/2008 | Amisar et al. |
| 2009/0005743 A1 | 1/2009 | Vaillancourt |
| 2009/0012480 A1 | 1/2009 | Moulton |
| 2009/0048566 A1 | 2/2009 | Ferguson |
| 2009/0054852 A1 | 2/2009 | Takano |
| 2009/0082732 A1 | 3/2009 | Hillman |
| 2009/0088696 A1 | 4/2009 | Harding |
| 2009/0093771 A1 | 4/2009 | Hwang |
| 2009/0131872 A1 | 5/2009 | Popov |
| 2009/0131876 A1 | 5/2009 | Coyne |
| 2009/0137958 A1 | 5/2009 | Erskine |
| 2009/0143737 A1 | 6/2009 | Kobayashi |
| 2009/0157013 A1 | 6/2009 | Wong |
| 2009/0163861 A1* | 6/2009 | Carlyon ................ 604/110 |
| 2009/0171285 A1 | 7/2009 | Wang |
| 2009/0177167 A1 | 7/2009 | Kuracina |
| 2009/0182280 A1 | 7/2009 | Glowacki |
| 2009/0216153 A1 | 8/2009 | Srivatsa |
| 2009/0216201 A1 | 8/2009 | Meehan |
| 2009/0221961 A1 | 9/2009 | Tal et al. |
| 2009/0227956 A1 | 9/2009 | Emmott |
| 2009/0281499 A1 | 11/2009 | Harding |
| 2009/0281506 A1 | 11/2009 | Mathias |

(56) References Cited

U.S. PATENT DOCUMENTS

| | | |
|---|---|---|
| 2009/0287154 A1 | 11/2009 | Harding |
| 2009/0292260 A1 | 11/2009 | Vaillancourft |
| 2009/0292261 A1 | 11/2009 | Greene |
| 2009/0306591 A1 | 12/2009 | Amisar |
| 2009/0312711 A1 | 12/2009 | Brimhall |
| 2010/0063455 A1 | 3/2010 | Moyer |
| 2010/0069840 A1 | 3/2010 | Suresh |
| 2010/0082002 A1 | 4/2010 | Baid |
| 2010/0087787 A1 | 4/2010 | Woehr |
| 2010/0094171 A1 | 4/2010 | Conway et al. |
| 2010/0106092 A1 | 4/2010 | Tanabe |
| 2010/0114035 A1 | 5/2010 | Schubert |
| 2010/0114036 A1 | 5/2010 | Steyn |
| 2010/0137803 A1 | 6/2010 | Funamura |
| 2010/0137815 A1 | 6/2010 | Kuracina |
| 2010/0191188 A1 | 7/2010 | Harding |
| 2010/0191189 A1 | 7/2010 | Harding |
| 2010/0198152 A1 | 8/2010 | Haindl |
| 2010/0204652 A1 | 8/2010 | Morrissey |
| 2010/0204654 A1 | 8/2010 | Mulholland |
| 2010/0222739 A1 | 9/2010 | Klippenstein |
| 2010/0222745 A1 | 9/2010 | Burkholz |
| 2010/0222746 A1 | 9/2010 | Burkholz |
| 2010/0222749 A1* | 9/2010 | Baid ............................. 604/263 |
| 2010/0228197 A1 | 9/2010 | Murashita |
| 2010/0234804 A1 | 9/2010 | Hiejima |
| 2010/0241087 A1 | 9/2010 | Moulton |
| 2010/0249707 A1 | 9/2010 | Woehr |
| 2010/0286611 A1 | 11/2010 | Schraga |
| 2010/0298770 A1 | 11/2010 | Rubinstein |
| 2010/0324484 A1 | 12/2010 | Smith |
| 2010/0331781 A1 | 12/2010 | Millerd |
| 2011/0015573 A1 | 1/2011 | Maan |
| 2011/0015579 A1 | 1/2011 | Swisher |
| 2011/0024664 A1 | 2/2011 | Burnard |
| 2011/0054398 A1 | 3/2011 | Djordjevic |
| 2011/0054402 A1 | 3/2011 | Tanabe |
| 2011/0054403 A1 | 3/2011 | Tanabe |
| 2011/0060286 A1 | 3/2011 | Tanabe |
| 2011/0060294 A1 | 3/2011 | Baid |
| 2011/0066107 A1 | 3/2011 | Stephens |
| 2011/0066197 A1 | 3/2011 | Jaax |
| 2011/0092914 A1 | 4/2011 | Clayson |
| 2011/0098641 A1 | 4/2011 | Haider |
| 2011/0118673 A1 | 5/2011 | Dringenberg |
| 2011/0125056 A1 | 5/2011 | Merchant |
| 2011/0152782 A1 | 6/2011 | Jones |
| 2011/0152832 A1 | 6/2011 | Foshee |
| 2011/0160662 A1 | 6/2011 | Stout |
| 2011/0160663 A1 | 6/2011 | Stout |
| 2011/0160675 A1 | 6/2011 | Ruan |
| 2011/0208124 A1 | 8/2011 | Rhad |
| 2011/0208126 A1 | 8/2011 | Riemelmoser |
| 2011/0208133 A1 | 8/2011 | Woehr |
| 2011/0213307 A1 | 9/2011 | Kawai |
| 2011/0264037 A1 | 10/2011 | Foshee |
| 2011/0264040 A1 | 10/2011 | Li |
| 2011/0275991 A1 | 11/2011 | Thayer |
| 2011/0282285 A1 | 11/2011 | Blanchard |
| 2011/0282286 A1 | 11/2011 | Argentine |
| 2011/0301542 A1 | 12/2011 | Schwartz |
| 2011/0301551 A1 | 12/2011 | Koehler |
| 2011/0319820 A1 | 12/2011 | Teoh |
| 2012/0016301 A1 | 1/2012 | Stout |
| 2012/0016302 A1 | 1/2012 | Stout |
| 2012/0022498 A1 | 1/2012 | Smith |
| 2012/0035552 A1* | 2/2012 | Woehr .......................... 604/246 |
| 2012/0041374 A1 | 2/2012 | Lee |
| 2012/0046620 A1 | 2/2012 | Woehr |
| 2012/0046621 A1 | 2/2012 | Vaillancourt |
| 2012/0059323 A1 | 3/2012 | Moberg |
| 2012/0059325 A1 | 3/2012 | Cluff |
| 2012/0078200 A1 | 3/2012 | Woehr |
| 2012/0130321 A1 | 5/2012 | Woehr |
| 2012/0136311 A1* | 5/2012 | Knutsson et al. ......... 604/164.08 |
| 2012/0143138 A1 | 6/2012 | King |
| 2012/0143151 A1 | 6/2012 | Low |
| 2012/0184910 A1 | 7/2012 | Woehr |
| 2012/0197201 A1 | 8/2012 | Tanabe |
| 2012/0215179 A1 | 8/2012 | Halili |
| 2012/0220956 A1 | 8/2012 | Kuracina |
| 2012/0220957 A1 | 8/2012 | Kuracina |
| 2012/0277679 A1 | 11/2012 | Steube |
| 2013/0030370 A1 | 1/2013 | Walker |
| 2013/0030371 A1* | 1/2013 | Knutsson ................. 604/164.08 |
| 2013/0079720 A1 | 3/2013 | Finnestad et al. |
| 2013/0096504 A1 | 4/2013 | Walker et al. |
| 2013/0245567 A1 | 9/2013 | Tremblay |

FOREIGN PATENT DOCUMENTS

| | | |
|---|---|---|
| EP | 0747085 | 12/1996 |
| JP | 2003/199822 | 7/2003 |
| JP | 2005/237638 | 9/2005 |
| WO | WO 92/18182 | 10/1992 |
| WO | WO 03/011381 | 2/2003 |
| WO | WO 2009/142878 | 11/2009 |
| WO | WO 2010/061405 | 6/2010 |
| WO | WO 2011/036574 | 3/2011 |
| WO | WO 2011/154767 | 12/2011 |
| WO | WO 2012/014018 | 2/2012 |

OTHER PUBLICATIONS

International Search Report dated Nov. 2, 2012 in International Application No. PCT/US2012/04839.

International Search Report dated Dec. 17, 2012 in International Application No. PCT/2012/055295.

International Search Report dated Dec. 19, 2012 in International Application No. PCT/US2012/056979.

International Search Report dated Jan. 16, 2013 in International Application No. PCT/US2012/060240.

* cited by examiner

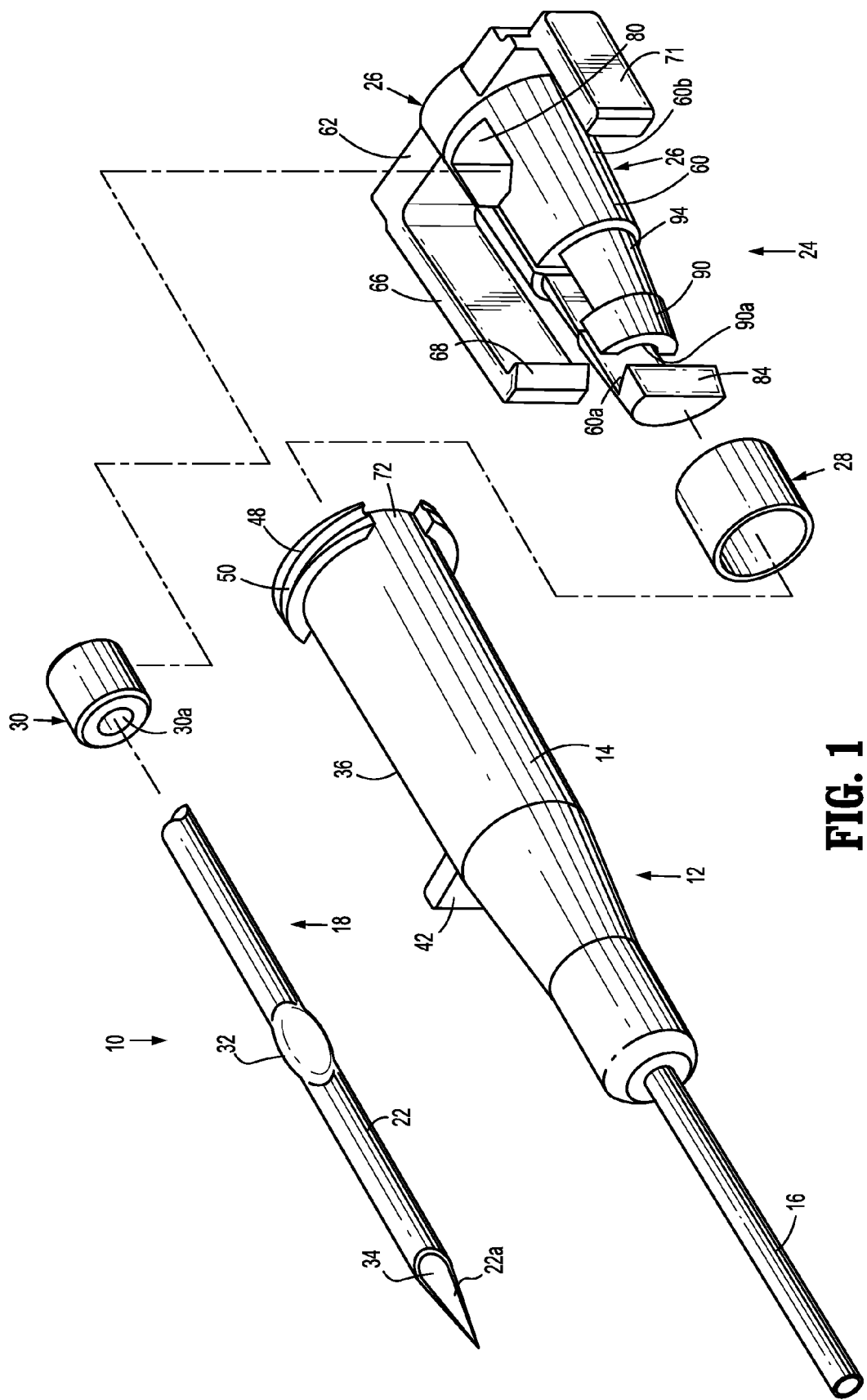

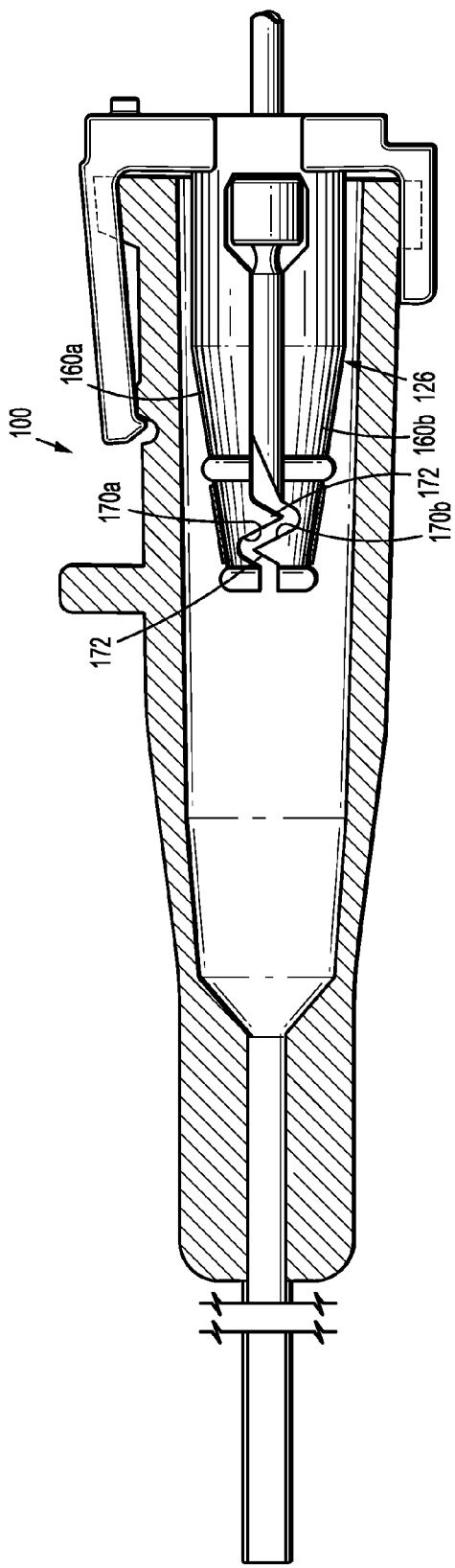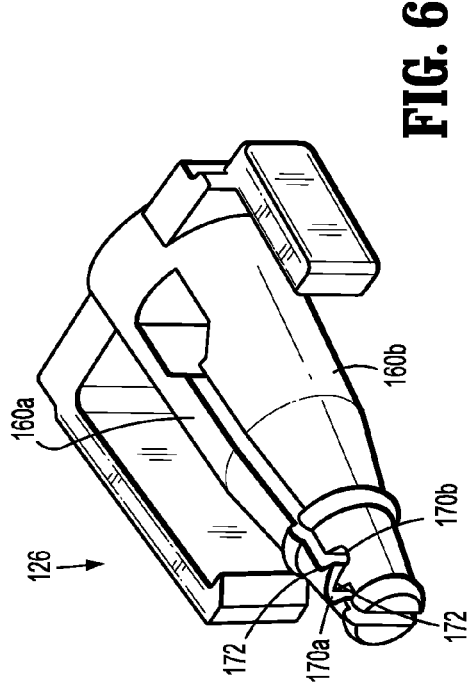
FIG. 5
FIG. 6

SAFETY IV CATHETER ASSEMBLIES

CROSS REFERENCE TO RELATED APPLICATIONS

This application is a continuation of U.S. patent application Ser. No. 13/457,550, filed Apr. 27, 2012 which claims priority to and the benefit of U.S. Provisional Application Ser. No. 61/479,556 entitled SAFETY IV CATHETER filed on Apr. 27, 2011 both of which are incorporated by reference herein in their entirety for all purposes.

BACKGROUND

1. Technical Field

The present disclosure relates to intravenous (IV) catheter assemblies for accessing a body vessel, and more particularly to IV catheter assemblies including a safety device for protecting a clinician from accidental needle stick injuries.

2. Background of Related Art

Intravenous (IV) catheter assemblies are utilized in a variety of medical applications for supplying or withdrawing fluid to or from a body vessel. Generally, IV catheter assemblies include an external cannula for indwelling in a blood vessel of a patient and an internal needle that is inserted into the external cannula to facilitate piercing of the blood vessel of the patient. In operation of the IV catheter assembly, the internal needle is inserted into the external cannula such that the tip portion of the internal needle protrudes from a tip portion of the external cannula. Next, the internal needle is manipulated to pierce a blood vessel and to position the external cannula within the blood vessel. While the external cannula is positioned within in the blood vessel, the internal needle is withdrawn from the external cannula leaving the external cannula positioned within the blood vessel. In this position, a medical device can be connected to the rear end portion of the external cannula using, for example, a luer connector, to facilitate the supply and withdrawal of fluid, such as blood, medication and/or nutrients to or from the body vessel.

After the internal needle is withdrawn from the external cannula, the exposed needle tip of the internal needle creates a danger of accidental needle stick injury which can leave a clinician vulnerable to the transmission of various blood-borne pathogens, such as HIV and hepatitis. While needle tip protectors have been developed to protect the clinician from needle stick injuries, the cost, ease of use, and effectiveness of these needle tip protectors leaves room for improvement.

Accordingly, it would be beneficial to provide a safety IV catheter assembly which is easily activated by a clinician, effectively protects a clinician from accidental needle stick injury and is economical to produce.

SUMMARY

The present disclosure is directed to a safety IV catheter assembly which comprises a catheter assembly including a catheter hub defining a cavity and a catheter tube, a needle assembly including a needle hub and a needle having an enlarged diameter portion and a needle tip, and a needle guard assembly including a needle guard having a body portion including a proximal wall defining a guard bore and first and second legs extending distally from the proximal wall. At least one of the legs has a radially extending portion and the first and second legs are movable from an unguarded position wherein the needle is positioned between the first and second legs and a guarded position wherein the radially extending portion is positioned distally of the needle tip to obstruct distal movement of the needle. The needle guard assembly further includes a bushing defining a bushing bore dimensioned to be slidably positioned about the needle at a location proximally of the enlarged diameter portion. An inner diameter of the bushing bore is smaller than the outer diameter of the enlarged diameter portion of the needle to prevent passage of the enlarged diameter portion of the needle through the bushing bore. The outer diameter of the bushing is greater than the inner diameter of the guard bore to prevent withdrawal of the needle through the guard bore.

In one embodiment, the first and second legs define a recess dimensioned to receive the bushing such that the bushing bore is aligned with the guard bore to slidably receive the needle. The recess may be configured to limit axial movement of the bushing about the needle in relation to the needle guard.

In one embodiment, the radially extending portion of the first leg is positioned distally of the distal end of the second leg. In addition, the second leg may be configured and dimensioned to be in spaced relation to the needle as the needle is withdrawn from the catheter assembly and the needle guard moves from the unguarded position to the guarded position.

In one embodiment, the needle guard assembly includes a biasing member positioned to urge the needle guard towards the guarded position. The needle guard may also be formed of a resilient material, wherein the needle guard is in an unbiased state in the guarded position. The biasing member may include an annular, resilient band.

In one embodiment, the needle guard includes an engagement arm which extends distally from the proximal wall and is configured to releasably engage the catheter hub.

In other embodiments, the first and second legs define an annular recess configured to receive the biasing member.

The first and second legs may define an undulating surface, wherein each of the undulating surfaces defines a radially extending portion.

BRIEF DESCRIPTION OF THE DRAWINGS

Various embodiments of the presently disclosed safety IV catheter assembly will be described herein with references to the accompanying drawings, wherein:

FIG. 1 is a side perspective view with parts separated of one embodiment of the presently disclosed safety IV catheter assembly;

FIG. 5 is a side, cross-sectional view of an alternate embodiment of the presently disclosed safety IV needle assembly with the needle tip withdrawn into the safety clip in the guarded position; and FIG. 6 is a perspective view of the safety clip of the safety IV catheter assembly shown in FIG. 5.

DETAILED DESCRIPTION OF EMBODIMENTS

Figure 1A:
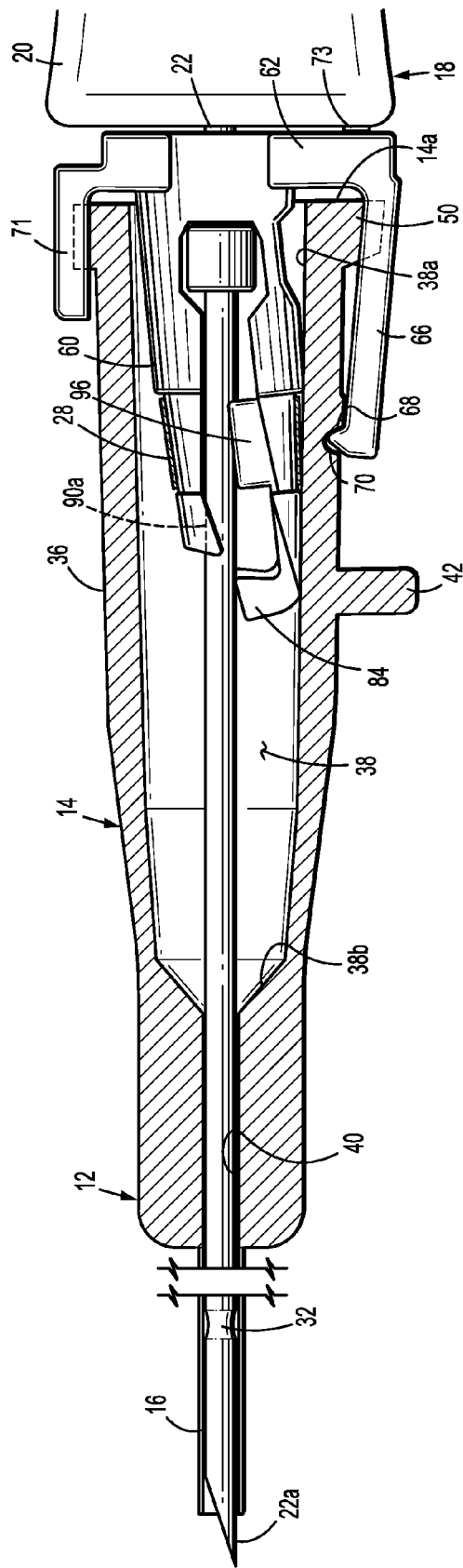
FIG. 1A is a side cross-sectional view of the safety IV catheter assembly shown in FIG. 1 in an assembled configuration.

Embodiments of the presently disclosed safety IV catheter assembly will now be described in detail with reference to the drawings wherein like reference numerals designate identical or corresponding elements in each of the several views. In this description, the term "proximal" is generally used to refer to the portion of the device that is closer to a clinician, while the term "distal" is generally used to refer to the portion of the device that is farther from the clinician.

FIG. 1 illustrates one embodiment of the presently disclosed safety intravenous (IV) catheter assembly shown generally as 10. Safety IV catheter assembly 10 includes a catheter assembly 12 including a catheter hub 14 and a catheter tube 16 extending distally from catheter hub 14, a needle assembly 18 including a needle hub 20 (FIG. 1A) and a needle 22 extending distally from needle hub 20, and a needle guard assembly 24 including a needle guard 26, a biasing member 28, and a bushing 30.

Referring to FIGS. 1 and 1A, needle 22 of needle assembly 18 includes a needle tip 22a and an enlarged diameter portion 32. Enlarged diameter portion 32 may be formed on needle 22 by crimping. Alternately, the enlarged diameter portion 32 may be formed on needle 22 using other known techniques including welding a ring or bead onto or about the needle 22. Needle 22 defines a fluid channel 34 which communicates the distal end of the needle 22 with the needle hub 20.

Catheter hub 14 includes a body 36 defining a cavity 38 (FIG. 1A) having an open proximal end 38a and a distal end 38b which communicates with a fluid channel 40. Channel 40 communicates with catheter tube 16 such that catheter tube 16 is in fluid communication with cavity 38 of body 36 of catheter hub 14.

Body 36 includes a radial protrusion 42 which is positioned on a central portion of body 36 at a location to be engaged by a clinician's finger as will be discussed in further detail below. A proximal end of body 36 includes structure 48 for engaging a medical device. In one embodiment, the engagement structure includes a luer connector 50 or the like.

Figure 1B:
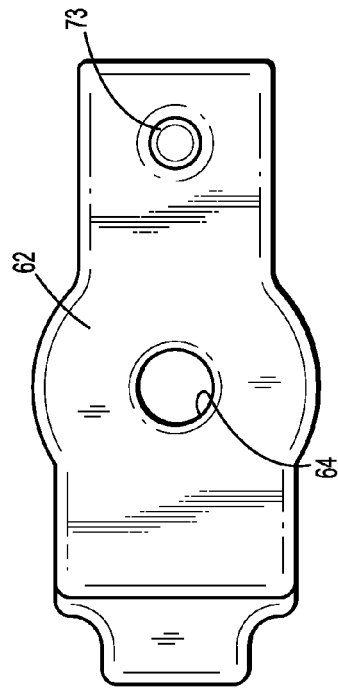
FIG. 1B is a rear end view of the safety clip of the safety IV catheter assembly shown in FIG. 1.
Figure 2:
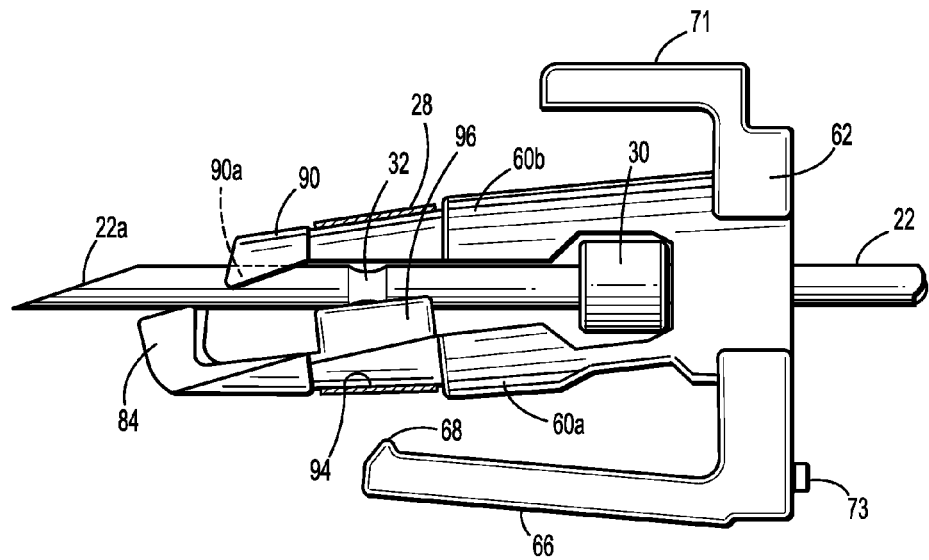
FIG. 2 is a side view of the safety clip and distal end of the needle of the safety IV catheter assembly shown in FIG. 1 with the needle tip in an unguarded position and the biasing member shown in cross-section.

As shown in FIGS. 1-2, needle guard assembly 24 is formed from a resilient material and includes needle guard 26, biasing member 28 and bushing 30. Needle guard 26 includes a split body portion 60 which defines a first leg 60a and a second leg 60b which extend distally from a proximal wall 62. Proximal wall 62 defines a proximal throughbore 64 (FIG. 1B). A projection 73 extends proximally from proximal wall 62 and is dimensioned to be received within a recess (not shown) formed in a distal face of the needle hub 20 to properly orient the needle hub 20 and the guard. A resilient engagement arm 66 is spaced from body portion 60 and extends distally from proximal wall 62 and is angled towards body portion 60. See FIG. 1A. A distal end of arm 66 includes a radially extending protrusion 68 which is positioned to be received in a recess 70 (FIG. 1A) formed in catheter hub 14 to releasably secure needle guard 26 to catheter hub 14 as will be discussed in further detail below. A locator arm 71 is also provided and extends distally from proximal wall 62. The locator arm 71 is located in diametrical opposition to engagement arm 66 and is positioned to be received within a channel 72 (FIG. 1) formed through luer connector 50 of catheter hub 14 to properly orient the needle guard 26 within the cavity of the catheter hub as will be discussed in further detail below. Similarly, engagement arm 66 is also positioned to extend through a separate channel 72 formed through luer connector 50 to assist in properly orienting needle guard 26 in relation to catheter hub 14.

Needle guard 26 defines a centrally located recess 80 between first leg 60a and second leg 60b. The recess 80 is dimensioned to receive the bushing 30 such that a bore 30a defined through bushing 30 is aligned with the proximal throughbore 64 in the proximal wall 62 of needle guard 26. Recess 80 may be dimensioned to axially contain or limit axial movement of bushing 30 in relation to safety clip 26. Bore 30a of bushing 30 and throughbore 64 of proximal wall 62 of needle guard 26 are dimensioned to slidably receive needle 22 but to prevent passage of enlarged diameter portion 32 of needle 22. More specifically, the inner diameters of bore 30a and throughbore 64 are larger than the outer diameter of needle 22 but smaller than the outer diameter of enlarged diameter portion 32 of needle 32. In addition, the outer diameter of bushing 30 is greater than the inner diameter of throughbore 64 of proximal wall 62 of needle guard 26. Bushing 30 may be formed of any material having sufficient strength to engage the enlarged portion of the needle tip and to provide sufficient slip as the needle moves through the bushing bore. In one embodiment, the busing may be formed of a metal, such as stainless steel.

Figure 4:
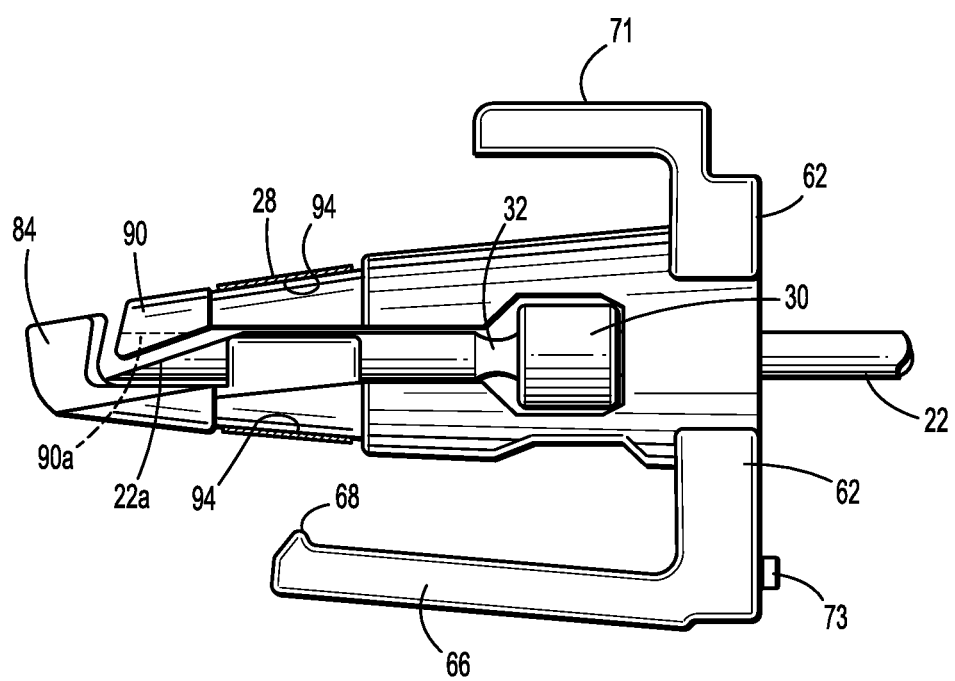
FIG. 4 is a side view of the safety clip and distal end of the needle of the safety IV catheter assembly shown in FIG. 1 with the needle tip in the guarded position and the biasing member shown in cross-section.

First leg 60a of needle guard 26 extends distally beyond second leg 60b and includes a radially extending portion 84. In one embodiment, radially extending portion 84 extends to a position distally of a distal end of second leg 60b when needle guard 26 is in guarded state (FIG. 4), i.e., in the state where the first leg 60a is not biased outwardly by needle 22 extending through the needle guard 26 and rather is moved inwardly by the inherent resilience of the needle guard 26 and the biasing member 28 as will be discussed in further detail below. Alternatively, the radially extending portion 84 need only extend radially a distance sufficient to prevent distal movement of the needle tip past the radially extending portion 84 after the needle tip 22a has been withdrawn into the needle guard 26 to the guarded position (FIG. 4).

As illustrated in FIGS. 1 and 1A, the second leg 60b of the needle guard 26 includes a distal end 90 which is spaced proximally of radially extending portion 84 of first leg 60a and defines a concavity 90a. The inner surface of second leg 60b is configured to be spaced from needle 22 to minimize the drag on the needle 22 during withdrawal of the needle 22 from catheter assembly 12. The length of second leg 60b should be such that when the needle 22 is fully retracted, the needle tip 22a extends distally of distal end 90 of second leg 60b. See FIG. 3.

First and second legs 60a and 60b define an annular recess 94 which is configured to receive biasing member 28. Although biasing member 28 is illustrated as a resilient, annular band, other biasing member configurations are envisioned. For example, the first leg 60a may include an embedded resilient strip formed of spring steel or the like to enhance the resilience of leg 60a.

Referring to FIGS. 1A and 2, one or more guide walls 96 may be provided on one or both of legs 60a and 60b to prevent needle 22 from becoming misaligned with needle guard 26. As illustrated, guide wall 96 is positioned on the first leg 60a to extend along a side of needle 22 at a position spaced from needle 22. Additional guide walls 96 may be provided to retain needle 22 and tip 22a in a guarded position between legs 60a and 60b.

Referring to FIG. 1A, in an assembled state, the needle guard 26 is supported on the proximal end of the catheter hub 14 such that the body portion 60 is positioned within cavity 38 and the proximal wall 62 of needle guard 26 is positioned adjacent to a proximal surface 14a of the catheter hub 14. With the body portion 60 of needle guard 26 positioned in cavity 38, engagement arm 66 and locator arm 71 extend through channels 72 in luer connector 50. Locator arm properly aligns needle guard 26 with catheter hub 14 and engagement arm 66 releasably secures needle guard 26 to catheter hub 14 via engagement of protrusion 68 within recess 70 of catheter hub 14.

In the assembled state, needle 22 extends through throughbore 64 (FIG. 1B) of proximal wall 62 of needle guard 26, between first and second legs 60a and 60b, and through the catheter assembly 12 such that the needle tip 22a extends from a distal end of catheter tube 16. In this position, the radially extending portion 84 of the first leg 60a is deflected outwardly from its unbiased position via engagement with the needle 22 such that the needle 22 passes between legs 60a and 60b. As discussed above, in one embodiment, the second leg 60b is spaced from the needle 22 to minimize any drag on the needle 22. As clearly shown in FIGS. 1A and 2, biasing member 28 is positioned about legs 60a and 60b of safety clip to urge the legs 60a and 60b towards each other to a guarded position. In an alternative embodiment, the biasing member may not be provided such that only the inherent resilience of the leg 60a urges leg 60a towards the guarded position (FIG. 4).

Figure 3:
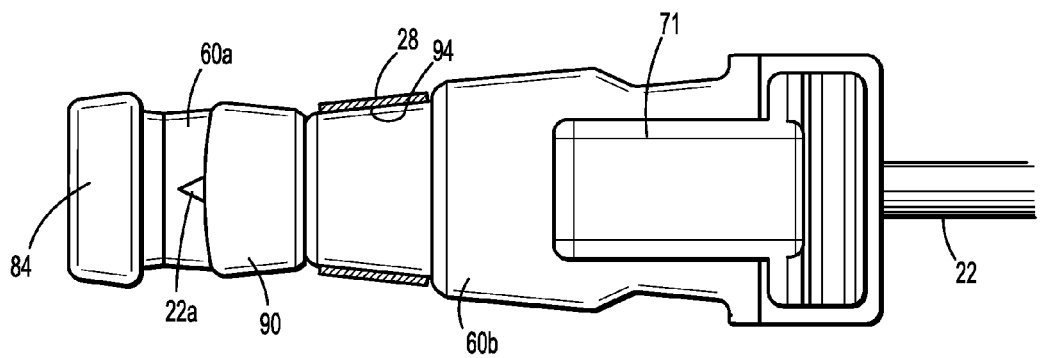
FIG. 3 is a top view of the safety clip and needle shown in FIG. 2 with the needle in a guarded position and the biasing member shown in cross-section.
Figure 4A:
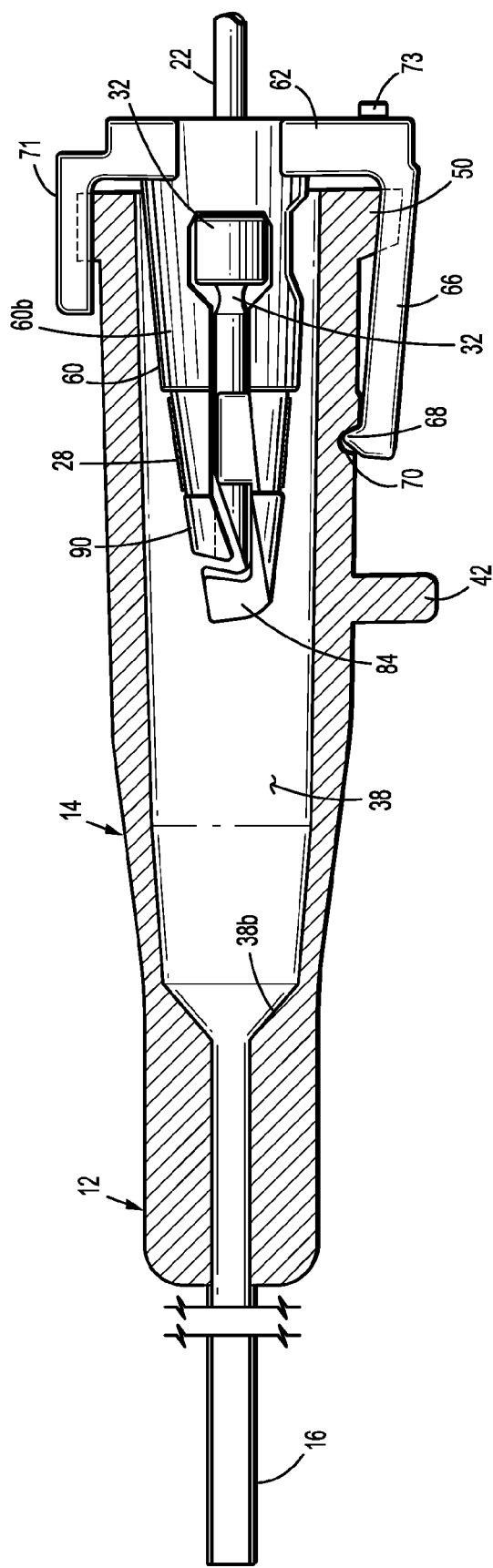
FIG. 4A is a side, cross-sectional view of the safety IV catheter assembly shown in FIG. 1A with the needle tip withdrawn into the safety clip in a guarded position.

Referring to FIGS. 3-4A, when the needle 22 is withdrawn from the catheter assembly 12 such that the needle tip 22a passes proximally of radially extending portion 84, the inherent resilience of the leg 60a and/or the urging of the biasing member 28 causes the leg 60a to move inwardly towards leg 60b to position radially extending portion 84 distally of needle tip 22a of needle 22. In this position, the radially extending portion 84 prevents distal movement of needle 22 in relation to needle guard 26. In addition, as needle 22 is withdrawn through needle guard 26, enlarged diameter portion 32 of needle 22 engages bushing 30 as the needle 22 slidably moves through the bore 30a of bushing 30 and through throughbore 64 (FIG. 1B) in proximal wall 62 of needle guard 26, to effect proximal movement of bushing 30 towards proximal wall 62. When bushing 30 engages proximal wall 62, further proximal movement of needle 22 in relation to needle guard 26 is prevented. More specifically, because the enlarged diameter portion 32 of needle 22 has a diameter greater than the inner diameter of bore 30a of bushing 30, and the outer diameter of bushing 30 is greater than the inner diameter of throughbore 64 in the proximal wall 62 of needle guard 26, further proximal movement or withdrawal of needle 22 from needle guard 26 is prevented when bushing 30 engages proximal wall 62. As such, when bushing 30 engages proximal wall 62 and radially extending portion 84 of leg 60a is positioned distally of needle tip 22a, the needle tip 22a is retained in a guarded position within the needle guard 26. As shown in FIGS. 3 and 4, in the guarded position, the distal end of the needle tip 22a extends distally beyond the distal end of the leg 60b. Alternately, needle tip 22a can be positioned proximally of the distal end of leg 60b in the guarded position. Bushing 30 may be formed of any material having sufficient strength to engage the enlarged portion of the needle tip and the proximal wall and to provide sufficient slip as the needle moves through the bushing bore. In one embodiment, the busing may be formed of a metal, such as stainless steel.

Referring to FIGS. 5 and 6, in an alternative embodiment of the presently disclosed safety IV catheter assembly shown generally as 100, the needle guard 126 is substantially similar to needle guard 26 except that the configuration of legs 160a and 160b of body 160 has been changed. More specifically, needle guard 126 includes a split body portion 160 including legs 160a and 160b. Legs 160a and 160b each define an undulating surface 170a and 170b, respectively. Each undulating surface 170a and 170b includes a radially extending portion 172. Each radially extending portion slidably engages the needle 122 when the needle 122 is positioned through the needle guard 126. When the needle 122 is positioned through the needle guard 126, legs 160a and 160b are deflected outwardly to facilitate passage of the needle 122. When the needle tip 122a is withdrawn through the needle guard 126 to a position in which the needle tip 122a is positioned proximally of the radially extending portions 172, such as shown in FIG. 5, the radially extending portions 172 are positioned to block distal movement of the needle 122. In all other respects, needle guard 126 functions in the same manner as needle guard 26.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A safety IV catheter assembly comprising:
a catheter assembly including a catheter hub and a catheter tube, the catheter hub defining a cavity;
a needle assembly including a needle hub and a needle, the needle having a needle tip; and
a needle guard assembly including a needle guard having a body portion including a proximal wall defining a guard bore dimensioned to slidably receive the needle and first and second legs extending distally from the proximal wall, and a radially extending portion formed on one end of the first leg, wherein in an assembled state of the safety IV catheter assembly, the needle extends between the first and second legs of the body portion of the needle guard and through the catheter assembly such that the needle tip extends from the catheter tube, and in a withdrawn state of the safety IV catheter assembly, the needle tip is positioned proximally of the radially extending portion of the first leg such that the radially extending portion obstructs distal movement of the needle, the second leg portion being in spaced relation to the needle in an unbiased state as the needle is withdrawn from the catheter assembly to minimize drag on the needle.

2. The catheter assembly of claim 1, wherein the radially extending portion of the first leg is positioned distally of the distal end of the second leg in the withdrawn state.

3. A safety IV catheter assembly comprising:
a catheter assembly including a catheter hub and a catheter tube, the catheter hub defining a cavity;
a needle assembly including a needle hub and a needle, the needle having a needle tip; and
a needle guard assembly including a needle guard having a body portion including a proximal wall defining a guard bore dimensioned to slidably receive the needle and first and second legs extending distally from the proximal wall, a radially extending portion formed on one end of the first leg, and a guide wall positioned on at least one of the first and second legs, wherein in an assembled state of the safety IV catheter assembly, the needle extends between the first and second legs of the body portion of the needle guard and through the catheter assembly such that the needle tip extends from the catheter tube, and in a withdrawn state of the safety IV catheter assembly, the needle tip is positioned proximally of the radially extending portion of the first leg such that the radially extending portion obstructs distal movement of the needle and the guide wall is positioned along a side of the needle to retain the needle tip in a guarded position between the first and second legs, wherein in the withdrawn state, the needle tip extends distally of a distal end of the second leg.

4. The catheter assembly of claim 1, wherein the distal end of the second leg defines a concavity.

5. The catheter assembly of claim 1, wherein the second leg includes a radially extending portion.

6. The catheter assembly of claim 5, wherein the first and second legs each define an undulating surface.

7. A safety IV catheter assembly comprising: a catheter assembly including a catheter hub and a catheter tube, the catheter hub defining a cavity;
a needle assembly including a needle hub and a needle, the needle having a needle tip; and
a needle guard assembly including a needle guard having a body portion including a proximal wall defining a guard bore dimensioned to slidably receive the needle and first and second legs extending distally from the proximal wall, and a radially extending portion formed on one end of the first leg, wherein in an assembled state of the safety IV catheter assembly, the needle extends between the first and second legs of the body portion of the needle guard and through the catheter assembly such that the needle tip extends from the catheter tube, and in a withdrawn state of the safety IV catheter assembly, the needle tip is positioned proximally of the radially extending portion of the first leg such that the radially extending portion obstructs distal movement of the needle, the second leg portion being in spaced relation to the needle in an unbiased state as the needle is withdrawn from the catheter assembly to minimize drag on the needle, wherein the second leg includes a radially extending portion, and the first and second legs each define an undulating surface,
wherein each of the undulating surfaces defines one of the radially extending portions of the first and second legs.

8. The catheter assembly of claim 3, wherein the radially extending portion of the first leg is positioned distally of the distal end of the second leg in the withdrawn state.

9. The catheter assembly of claim 3, wherein the distal end of the second leg defines a concavity.

10. The catheter assembly of claim 1, further including a guide wall positioned on at least one of the first and second legs.

* * * * *